(12) United States Patent
Kallmayer et al.

(10) Patent No.: US 8,741,321 B2
(45) Date of Patent: *Jun. 3, 2014

(54) CAPSULE WHOSE ENVELOPE IS SEPARATELY IMPERCEPTIBLE DURING THE TOPICAL USE THEREOF

(75) Inventors: Volker Kallmayer, Hamburg (DE); Jens Nielsen, Henstedt-Ulzburg (DE); Andreas Bleckmann, Hamburg (DE); Heidi Riedel, Hamburg (DE); Julia Eckert, Hamburg (DE); Thomas Raschke, Pinneberg (DE); Frank Teuber, Norderstedt (DE); Corinna Zu Putlitz, Bonningstedt (DE); Stephanie Conzelmann, Hamburg (DE); Kathrin Liste, Hamburg (DE); Uta Kruse, Hamburg (DE); Yvonne Eckharol, Hamburg (DE)

(73) Assignee: Beiersdorf AG, Hamburg (DE)

( * ) Notice: Subject to any disclaimer, the term of this patent is extended or adjusted under 35 U.S.C. 154(b) by 1350 days.

This patent is subject to a terminal disclaimer.

(21) Appl. No.: 10/569,382

(22) PCT Filed: Aug. 27, 2004

(86) PCT No.: PCT/EP2004/009563
§ 371 (c)(1),
(2), (4) Date: Oct. 4, 2006

(87) PCT Pub. No.: WO2005/020940
PCT Pub. Date: Mar. 10, 2005

(65) Prior Publication Data
US 2008/0089913 A1    Apr. 17, 2008

(30) Foreign Application Priority Data

Aug. 27, 2003 (DE) .................................. 103 39 747
Aug. 30, 2003 (DE) .................................. 103 40 106
Dec. 10, 2003 (DE) .................................. 103 57 639

(51) Int. Cl.
*A61K 8/11* (2006.01)
*A61Q 19/00* (2006.01)

(52) U.S. Cl.
USPC .......................... 424/401; 514/772.3; 424/502

(58) Field of Classification Search
USPC ................................. 424/401, 502; 514/772.3
See application file for complete search history.

(56) References Cited

U.S. PATENT DOCUMENTS 4,675,236 A    6/1987  Ohkawara et al.
4,880,634 A   11/1989  Speiser (Continued)

FOREIGN PATENT DOCUMENTS

CH          692968       1/2003
DE       3537748 A1      5/1986

(Continued)

OTHER PUBLICATIONS

Translation of WO 01/03538 from espacenet.com.*

(Continued)

*Primary Examiner* — Rachael E Bredefeld
(74) *Attorney, Agent, or Firm* — Abel Law Group, LLP

(57) ABSTRACT

A capsule for cosmetic and/or dermatological ingredients and processes for the production thereof. The capsule comprises an envelope which is solid, semisolid and/or dimensionally stable and comprises one or more substances which are selected from waxes, emulsifiers, and natural and synthetic polymers. The capsule may also comprise a filling.

44 Claims, 1 Drawing Sheet

(56) References Cited

U.S. PATENT DOCUMENTS

| | | | |
|---|---|---|---|
| 5,270,054 A | 12/1993 | Bertolini | |
| 5,650,166 A * | 7/1997 | Ribier et al. | 424/450 |
| 5,686,112 A | 11/1997 | Liedtke et al. | |
| 5,705,217 A | 1/1998 | Aasted | |
| 5,785,976 A | 7/1998 | Westesen et al. | |
| 5,885,486 A | 3/1999 | Westesen et al. | |
| 6,045,813 A * | 4/2000 | Ferguson et al. | 424/401 |
| 6,156,804 A | 12/2000 | Chevalier et al. | |
| 6,197,281 B1 * | 3/2001 | Stewart et al. | 424/59 |
| 6,207,178 B1 | 3/2001 | Westesen et al. | |
| 6,531,160 B2 | 3/2003 | Biatry et al. | |
| 6,534,091 B1 | 3/2003 | Garces et al. | |
| 6,818,296 B1 | 11/2004 | Garces et al. | |
| 6,823,649 B1 | 11/2004 | Pauchet | |
| 2002/0022038 A1 | 2/2002 | Biatry et al. | |
| 2002/0026771 A1 | 3/2002 | Brown | |
| 2002/0102282 A1 | 8/2002 | Bleckmann et al. | |
| 2003/0044469 A1 | 3/2003 | Viladot Petit et al. | |
| 2003/0064106 A1 | 4/2003 | Garces et al. | |
| 2004/0005283 A1 | 1/2004 | Cernasov et al. | |
| 2004/0223989 A1 | 11/2004 | Auguste et al. | |
| 2004/0258721 A1 | 12/2004 | Bauer et al. | |
| 2005/0191346 A1 | 9/2005 | Nowak et al. | |

FOREIGN PATENT DOCUMENTS

| | | |
|---|---|---|
| DE | 19852262 | 5/2000 |
| DE | 19945203 | 12/2000 |
| DE | 10059668 | 6/2002 |
| DE | 10149143 A1 | 4/2003 |
| DE | 10209111 | 9/2003 |
| DE | 10210449 | 9/2003 |
| DE | 202008001135 U1 | 8/2008 |
| EP | 0234078 | 9/1987 |
| EP | 0529396 | 3/1993 |
| EP | 0998910 | 5/2000 |
| EP | 1201219 | 5/2002 |
| EP | 1473016 | 11/2004 |
| JP | S5973510 A | 4/1984 |
| JP | 10-182337 | 7/1998 |
| JP | 2001-348310 | 12/2001 |
| JP | 2003-073230 | 3/2003 |
| WO | 9405248 A1 | 3/1994 |
| WO | 94/20072 | 9/1994 |
| WO | 9624328 A1 | 8/1996 |
| WO | 9735537 A1 | 10/1997 |
| WO | 00/10522 | 3/2000 |
| WO | 00/67728 | 11/2000 |
| WO | 01/03538 | 1/2001 |
| WO | 0103676 A1 | 1/2001 |
| WO | 01/38174 | 5/2001 |
| WO | 0185895 A1 | 11/2001 |
| WO | 03/075881 | 9/2003 |
| WO | 2005/020949 | 3/2005 |

OTHER PUBLICATIONS

"The HLB System: A Time-saving guide to emulsifier selection," pp. 1-22, 1980, ICI Americas.*
English Language Abstract of JP 2003-073230.
English Language Abstract of DE 102 09 111.
English Language Abstract of EP 1 201 219.
English Language Abstract of DE 100 59 668.
English Language Abstract of DE 199 45 203.
English Language Abstract of DE 198 52 262.
English Language Abstract of CH 692 968.
English Language Abstract of DE 198 46 772.
English Language Abstract of EP 0 529 396.
English Language Abstract of JP 10-182337.
English Language Abstract of JP 2001-348310.
U.S. Appl. No. 10/569,381 to Raschke et al., which is a National Stage Application of International Application PCT/EP/2004/009518.
Moderne Pharmazeutische Technologie 2009, Kapitel 1.8 "Weichkapseln".
Moderne Pharmazeutische Technologie 2009, Kapitel 1.8 "Hartkapseln".

* cited by examiner

CAPSULE WHOSE ENVELOPE IS SEPARATELY IMPERCEPTIBLE DURING THE TOPICAL USE THEREOF

CROSS-REFERENCE TO RELATED APPLICATIONS

The present application is a U.S. National Stage of International Application No. PCT/EP2004/009563, filed Aug. 27, 2004, which claims priority of German Patent Application No. 103 39 747.7, filed Aug. 27, 2003, German Patent Application No. 103 40 106.7, filed Aug. 30, 2003, and German Patent Application No. 103 57 639.8, filed Dec. 10, 2003.

BACKGROUND OF THE INVENTION

1. Field of the Invention

The invention relates to cosmetic and dermatological preparations in the form of capsules comprising an envelope which is solid, semisolid and/or dimensionally stable and consists essentially of waxes, emulsifiers, natural and/or synthetic polymers and/or mixtures thereof, and to the method for their production. Furthermore, the invention relates to a capsule with a filling consisting of one or more solid, semisolid, pasty and/or liquid ingredients. Optionally, the envelope may additionally comprise water and/or polyols.

The property of the envelope is characterized in that it
  melts upon rubbing and/or distributing the preparation on the skin and/or the hair and/or becomes completely or partially liquid due to shear forces
  and/or it dissolves in the filling and/or the skin sebum lipids or as a result of mixing internal phase and enveloping material
and is thus no longer perceptible for the user as a separate constituent of the preparation besides the filling.

2. Discussion of Background Information

The prior art discloses pharmaceutical capsules, for example soft and hard gelatin capsules, which consist of an envelope of gelatin and glycerol, and sometimes dyes, and a liquid, pasty or particulate filling. The method of producing these capsules known for many years takes place, for example, in accordance with the so-called rotary-die system (Seifen-Öl-Fette-Wachse, Vol. 113; No. 3/1987, page 67 ff). These gelatin capsules dissolve when swallowed in the gastrointestinal tract and release their ingredients. Since it is directly possible to produce capsules in different sizes and shapes, use is limited not just to peroral application forms (Rudolf Voigt, "Pharmazeutische Technologie" [Pharmaceutical Technology], Deutsche Apotheker Verlag, Stuttgart, 9th edition (2000), p. 543ff). Oral absorption can be achieved through suckable capsules. They are hollow on the inside and have a wall which is three times thicker than that of other capsules. The active ingredient is incorporated here in the gelatin envelope. A further example is nitroglycerol chewable capsules (bite-through capsules), which likewise allow rapid absorption of the active ingredient via the oral mucosa. Furthermore, individually dosed medicaments can be applied after puncturing or cutting the tubular ointment capsules by squeezing out the contents (percutaneous application of nitroglycerol heart ointment).

From the food sector, pralines, which comprise liquid or pasty ingredients in a dimensionally stable chocolate coating, for example, are known. The coating melts during sucking or biting through in the mouth or after swallowing.

In the cosmetics sector, the so-called bath beads are known whose envelope, e.g. made of gelatin, dissolves in hot or warm bathwater without leaving a residue and releases its contents, for example surfactant preparations, emulsions, lipids, dyes and/or perfumes, into the bathwater. Since the envelope consists of gelatin, the product must not contain water, otherwise the envelope would soften during storage.

A second group of cosmetic capsules covers all products for which the envelope represents only a container for the single dose and use and whose envelope is left behind following use. A disadvantage with this is that the envelope which is left behind is troublesome and in addition has to be disposed of.

Numerous cosmetic and/or dermatological active ingredients are unstable toward certain influences such as moisture, low or high pH values and oxygen or light. There has therefore been no lack of attempts to remove the specified undesired environmental influences from such active ingredients in such a way that the active ingredients are nevertheless released upon application. One way of achieving this aim 1s the microencapsulation or nanoencapsulation of active ingredients. The encapsulation material as carrier system for the active ingredients allows them to be incorporated into suitable preparations in a form protected against environmental influences without the user being able to perceive the capsules during product application.

The aim of such an encapsulation is, for example, to produce wax particles containing active ingredient in the micrometer range (1-250 μm) which can be incorporated into common pasty or liquid cosmetic preparations. It is hitherto not known to produce, store and topically use these microcapsules as an independent cosmetic preparation. DE 10210449 discloses wax-coated capsules which have a content of active ingredient. These capsules are produced by means of a so-called fluidized-bed process, meaning that, at most, capsules measuring 200 μm can be produced.

There are a number of approaches for encapsulating cosmetic active ingredients. For example, the liposomal encapsulation of medicaments, which is intended to lead to a slow release of active ingredient, is known. These are essentially spherical vesicles containing active ingredient and surrounded by phospholipids or other amphiphilic agents, the so-called liposomes. The long-term stability of such structures, however, is poor.

Nanoparticles are solid particles with particle sizes of from 20 to 500 nm. Sometimes, larger particles with diameters up to 1000 nm are also regarded as being nanoparticles. Particles of this type generally consist of polymers and have cavities or form a envelope so that guest molecules stay themselves on the inside, these molecules being enclosed or adsorbed. These guest molecules are then slowly released upon application of the nanoparticle-containing product. Solid lipid nanoparticles, which comprise active ingredients distributed within a matrix made of solid lipids behave in a similar way. The size of the particle is comparable with that of nanoparticles.

Numerous methods are known for encapsulating pharmaceutical or cosmetic active ingredients for controlling active ingredient release or the stable incorporation in preparations.

European patent application EP 1064911 or EP 1064912 discloses microcapsules comprising active ingredient and having a diameter of from 0.1 to 5 mm which are obtained by preparing a matrix from gel formers, chitosan and active ingredient, and adding this dropwise to aqueous solutions of anionic polymers. In so doing, a membrane forms from chitosan and anionic polymer and surrounds the active ingredient solution. These microparticles are then in turn used as constituent of customary cosmetic preparations. General information regarding encapsulation techniques with chitosan can be found in Journal of Microencapsulation 14, pages 689-711 (1997).

Mostly lipophilic active ingredients encapsulated in lipid particles are known per se to the person skilled in the art. For example, EP 167825, DE 100 59 668, DE 199 45 203, EP 0934743, WO 94/20072, WO 00/10522 and WO 00/67728 describe lipid particles charged with active ingredient. However, these documents were unable to solve the problem of providing capsule-like preparations with enclosed liquid, pasty or solid cosmetic ingredients and which can be prepared, stored and applied topically as an independent cosmetic preparation.

DE 19852262, DE 9321186 and CH 692968 disclose methods of producing confectionery, in particular chocolate articles, by the so-called one-shot, frozen-cone or cold-stamp method.

The methods described therein are concerned exclusively with the production of chocolate articles, pralines.

It is an object of the present invention to provide a cosmetic preparation which is in the form of a solid, semisolid or dimensionally stable capsule, is thus individually portionable and can be distributed as a whole on the skin. In particular, it is the object of the present invention to provide a cosmetic preparation which constitutes a novel cosmetic product form and offers the user a novel application experience and broadens the application spectrum of skin care and/or hair care products.

SUMMARY OF THE INVENTION

The present invention provides a capsule for cosmetic and/or dermatological ingredients. The capsule comprises an envelope which is solid, semisolid and/or dimensionally stable and comprises one or more substances which are selected from waxes, emulsifiers, and natural and synthetic polymers.

In one aspect, the envelope may be solid, semisolid and/or dimensionally stable up to a temperature of at least 35° C.

In another aspect, the envelope may comprise one or more substances which are selected from microcrystalline waxes, paraffin waxes, ester waxes, glyceride waxes, fatty alcohols and solid emulsifiers. By way of non-limiting example, the envelope may comprise one or more waxes selected from cetyl palmitate, cetyl ricinoleate, beeswax, hydrogenated cocoglycerides, methyl palmitate, methyl stearate, myristyl lactate, cetyl lactate, stearyl lactate, candelilla wax, carnauba wax, paraffin wax, ceresine, ozokerite, myristyl myristate, tripalmitin, tribehenin, glyceryl palmitostearate, hydrogenated rapeseed oil and C15-C40 alkylstearyl stearate. Preferably, the envelope comprises at least ceresine and/or ozokerite.

In another aspect, the envelope may comprise constituents or constituent combinations which have as sharp as possible melting points to allow the envelope to have a narrow melting range at about 30° C.

In yet another aspect, the envelope may further comprise water and/or one or more polyols. For example, the envelope may comprise from 50% to 60% by weight of water.

In a still further aspect, the envelope may comprise one or more substances which are selected from cellulose ethers, polyvinylpyrrolidone, polyacrylates, polymethacrylates, polyethylene, nylon and Eudragit.

In another aspect, the envelope may comprise lipids which are liquid at room temperature or liquid mixtures thereof, and the envelope may be solidified by having water droplets incorporated therein.

In another aspect, the envelope may comprise a dimensionally stable lipid/emulsifier mixture which comprises dispersed water with a droplet size below 50 micrometers.

In yet another aspect, the envelope may further comprise one or more surface-active substances such as, e.g., one or more W/O emulsifiers. By way of non-limiting example, the one or more W/O emulsifiers may comprise one or more emulsifiers which are selected from branched or unbranched, saturated or unsaturated fatty acids having 12 to 26 carbon atoms, polyglyceryl-3 diisostearate, polyglyceryl-4 isostearate, polyglyceryl-2 dipolyhydroxystearate, cetyl PEG/PPG-10-1-dimethicone, PEG-30 dipolyhydroxystearate, PEG-40 sorbitan perisostearate, cetyldimethicone copolyol, PEG-7 hydrogenated castor oil, PEG 45/dodecyl glycol copolymer, PEG 22/dodecyl glycol copolymer, pentaerythrityl isostearate, isostearyl diglyceryl succinate, sorbitan isostearate, polyglyceryl-2 sesquiisostearate, glyceryl isostearate, sorbitan stearate, glyceryl stearate, PEG-25 hydrogenated castor oil, PEG-40 sorbitan peroleate, sorbitan oleate, PEG-40 sorbitan periisostearate, polyglyceryl-3 oleate, polyglyceryl-2 sesquioleate and polyglyceryl-4 isostearate and beeswax.

In a still further aspect, the capsules of the present invention may have an average diameter of from 3 mm to 40 mm and/or the capsules may have a predominantly spherical, round or ellipsoidal shape with a volume of from 0.1 ml to 20 ml.

In another aspect, the envelope of the capsule of the present invention may have a thickness of from 0.001 mm to 3 mm, e.g., a thickness of from 0.01 mm to 2 mm.

In yet another aspect, the capsule of the present invention may comprise a filling.

The filling may comprise one or more substances which are selected from cosmetic and dermatological ingredients which are solid, semisolid, pasty and/or liquid. In one aspect, the envelope and/or the filling may comprise water. In another aspect, the filling may comprise one or more of an anhydrous preparation, an O/W, W/O or W/O/W emulsion, a gel, a hydrodispersion, a surfactant, and a microemulsion. Preferably, the filling comprises at least an O/W emulsion.

In yet another aspect, the envelope may comprise a W/O emulsion and/or a wax, and the filling may comprise one or more of an O/W emulsion, a hydrous composition, a hydrogel and a hydrocolloid.

In a still further aspect, the filling may comprise a detersive substance and/or a surfactant in solid or liquid form, and the envelope may comprise one or more waxes.

In another aspect, the envelope and/or the filling may further comprise one or more substances which are selected from auxiliaries, UV filters, pigments, active ingredients, dyes, sensory additives, thickeners, gel formers, preservatives, antioxidants, complexing agents, flavorings, denaturants, and perfumes.

In another aspect of the capsule of the present invention, the envelope thereof may melt upon rubbing and/or distributing it on the skin and/or the hair; and/or become completely or partially liquid due to shear forces; and/or dissolve in the filling and/or the skin sebum lipids and/or as a result of mixing filling and envelope materials, whereby it is no longer perceptible as a separate constituent of the capsule, particularly, besides the filling.

The present invention also provides a cosmetic and/or dermatological product which comprises one or a plurality of the capsules according to the present invention in a packaging. For example, a plurality of capsules may be packaged individually or in a number of two or more in a pack, made of paper, metal and/or plastic such as, e.g., a blister pack made of paper, metal and/or plastic. In one aspect, the capsules may be packaged in ready-made portions in a blister pack for individual removal. In another aspect, the capsules may be packaged in a dispenser system.

In another aspect of the cosmetic and/or dermatological product, the product may comprise at least two capsules which differ in their appearance, their ingredients and/or their purpose. For example, at least two capsules may differ at least in their color.

In another aspect of the cosmetic and/or dermatological product of the present invention, at least some of the capsules may be present individually enveloped with a film, paper and/or coating material in a common packaging.

The present invention also provides a process for making a filled capsule according to the present invention. The process comprises freezing the filling and immersing the frozen filling into molten envelope material which becomes solid at a temperature of 35° C. or higher or coating the filling material with envelope material in a Kugelcoater or spraying envelope material in liquefied form onto the filling by means of fluidized-bed procedures and thereafter solidifying the envelope material, whereby a solid or semisolid closed envelope is formed around the filling, and subsequently removing the formed capsule from the molten envelope material upon reaching the desired envelope thickness and shape.

The present invention also provides further processes for making a filled or unfilled capsule according to the present invention. A first process comprises producing a hollow sphere from molten envelope material and, optionally, filling the sphere through a hole in the wall thereof with filling material and thereafter sealing the hole by a plug of envelope material.

A second process comprises casting hollow hemispheres, optionally, filling the hemispheres individually, positioning the hollow hemispheres congruently with respect to one another and fusing them together by a thermal treatment.

A third process comprises providing two hemispheres, one or both having a filling hole for subsequent filling, welding the hemispheres together to form a hollow sphere and, optionally, filling the hollow sphere with a filling through the filling hole.

The present invention also provides processes for making a filled capsule according to the present invention. A first process comprises
- filling a first envelope mass through a first nozzle into a mold,
- pressing a chilled shaped body into the first envelope mass in the mold,
- shaping and cooling the first envelope mass,
- introducing a filling mass through a second nozzle,
- applying a second envelope mass through a third nozzle to form an envelope, where the first and third nozzles may be identical and/or the and first and second envelope masses may be identical,
- sealing the formed envelope and removing the finished capsule from the mold.

A second process for making a filled capsule according to the present invention comprises
- forming a mold from an upper half-mold and a lower half-mold, where the upper half-mold has an opening,
- inserting into the mold, through the opening in the upper half-mold, a twin nozzle which comprises an inner channel that is concentrically arranged in an outer channel,
- feeding envelope mass through the outer channel into the mold to form a continuous base of envelope mass,
- feeding filling mass through the inner channel into the mold, where during the feeding of the envelope mass and the filling mass the nozzle is moved upward out of the mold,
- stopping the feeding of the filling mass to allow the formation of a sealed envelope, and
- separating the two half-molds from one another to release the finished capsule.

A third process for making a filled capsule according to the present invention comprises
- providing a half-mold having an open upper surface or an upper opening;
- inserting into the half-mold, through the open surface or the opening, a twin nozzle which comprises an inner channel that is concentrically arranged in an outer channel,
- feeding envelope mass through the outer channel into the half-mold to form a continuous base of envelope mass,
- feeding a filling mass through the inner channel into the half-mold, where during the feeding of the envelope mass and the filling mass the nozzle is moved upward out of the half-mold,
- stopping the feeding of the filling mass to allow forming of a sealed envelope,
- releasing the finished capsule from the half-mold.

The present invention also provides a method of applying a cosmetic ingredient and/or and a dermatological ingredient to the skin. The method comprises rubbing and/or distributing on the skin the capsule of the present invention which comprises the desired cosmetic ingredient and/or dermatological ingredient. For example, the cosmetic ingredient and/or dermatological ingredient may be comprised in the envelope of the capsule, or the capsule may comprise a filling and the cosmetic ingredient and/or dermatological ingredient may be comprised in the filling, the envelope or both. In one aspect, the ingredient may be comprised in the filling or the filling and the envelope.

DETAILED DESCRIPTION OF THE INVENTION

Figure 1:
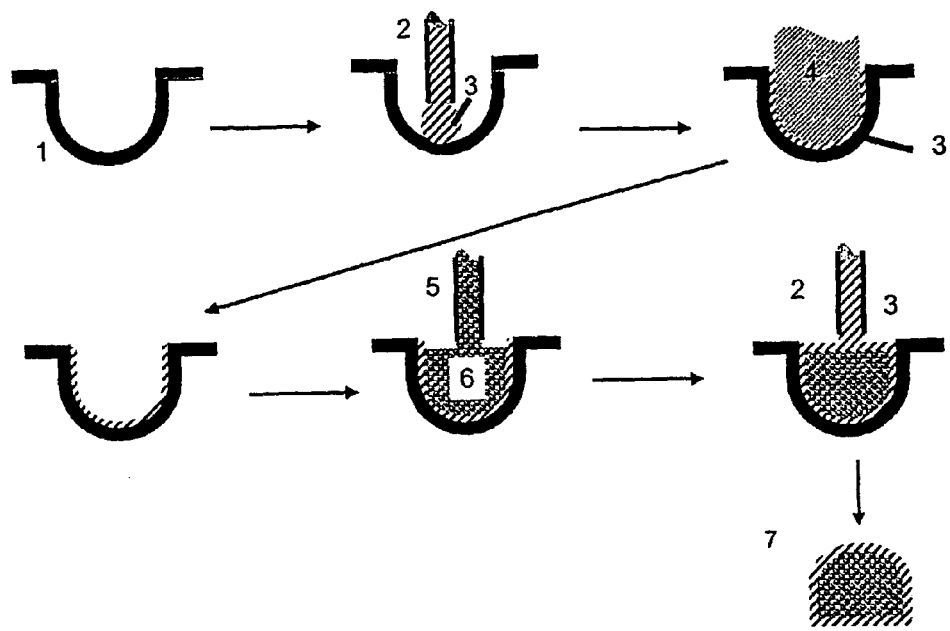
FIG. 1 shows a schematic representation which illustrates a process for making a filled capsule according to the present invention.

It was surprising and extraordinarily astonishing for the person skilled in the art that the set objects can be achieved by a cosmetic and/or dermatological capsule for cosmetic and/or dermatological ingredients comprising a capsule envelope which is solid, semisolid and/or dimensionally stable and consists essentially of waxes, emulsifiers, natural and/or synthetic polymers and/or mixtures thereof.

Preferably, the capsules comprises a filling consisting of one or more solid, semisolid, pasty and/or liquid ingredients. It is further preferred that the capsule envelope is solid, semisolid and/or dimensionally stable up to a temperature of at least 35° C.

Optionally, the capsule envelope additionally comprises water and/or polyols. The advantage and at the same time the property according to the invention of the capsule is that it
- melts upon rubbing and/or distributing on the skin and/or the hair and/or becomes completely or partially liquid due to shear forces and/or dissolves in the filling and/or the skin sebum lipids or as a result of mixing filling and envelope material and thus, particularly for the user, is no longer perceptible, particularly as a separate constituent besides the filling.

I.e., the capsule advantageously soaks in during application on the skin or the hair completely without leaving behind residues.

Compared, in particular, with known cosmetic capsules whose envelope stays behind following application, according to the invention, the capsule envelope can remain entirely on the skin, meaning that, for example, it is possible to incorporate active ingredients into the envelope. The capsule envelope can therefore make an active, caring contribution in the cosmetic and dermatological preparation and does not just serve as packaging.

Many terms such as "balls", "capsules" or "capsule-shaped preparation" can in principle be used to describe the capsules according to the invention although different meanings are sometimes assigned to these terms. In particular, the meaning of the term "capsule" is not limited here to the precisely defined shapes, preparation methods, ingredients and possible applications of the pharmaceutical preparations likewise termed "capsules", but does include these. In general, according to the invention, a capsule is a, for example, approximately round or ellipsoidal object which is clearly distinguishable from its surroundings and which, when pressed lightly and, for example, through touching when removing it from a packaging, does not change its shape. However, according to the invention, other shapes of capsules and/or of preparations are also conceivable provided the claimed features of the capsule, of the capsule envelope and of the filling are observed.

The capsule according to the invention comprises preportioned cosmetic products which consist of a solid or semisolid envelope and advantageously a filling. The term solid and semisolid according to the invention defines the state of the envelope, corresponding to pharmaceutical technology. The solid or semisolid envelope is ideally also referred to as dimensionally stable. However, a capsule with a colloquially speaking soft, wobbly or jelly-like envelope is also in accordance with the invention. The envelope breaks, melts and/or dissolves upon rubbing and dissolves if appropriate upon distribution with the ingredients of the filling on the skin or the hair. This ensures that a preparation can be applied, for example, as a cosmetic without undesired residues on the skin or the hair.

Compared with capsule-shaped preparations known from the prior art, no envelope material constituents of any kind are left behind unused on the skin, which constituents are unsightly, cause unnecessary costs and environmental burdens and, moreover, following product application have to be removed by the consumer.

The capsules according to the invention have a size, i.e. average diameter, of 3, preferably 5, up to 40 mm. The capsules can thus be handled and used individually. The capsule-shaped preparations according to the invention are dimensionally stable as dragees, capsules, balls or hollow balls during storage and removal and become liquid or dissolve only when distributed. This is achieved through a special combination of the envelope or in combination with the capsule material.

The capsule envelope must be solid, semisolid and/or dimensionally stable under storage conditions to which cosmetic products are usually subjected, i.e. the shape of the capsules according to the invention must not change during storage as a result, for example, of the effect of gravity or temperature up to 35° C. Ideally, the envelopes do not stick together during storage even if two capsules are in contact for a prolonged period. Should this requirement be technologically impractical, the problem can be solved through an individual packaging of each individual capsule, similar to an individual packing (candy paper).

Moreover, the envelope material must protect the filling from drying out during storage. This applies particularly if the filling comprises volatile substances, such as water, short-chain alcohols (e.g. ethanol, isopropanol), perfumes and fragrances or low-boiling oils (e.g. cyclomethicone).

The envelope material stays behind entirely on the skin following application. According to the invention, it is of great importance that all of the raw materials from which the envelope is constructed are very well tolerated by the skin. Ideally, they make a contribution to skin care, for example by enhancing the natural skin barrier and thus protecting the skin from drying out.

Moreover, the composition of the envelope has a decisive influence on the feel of the skin of the consumer when using the preparations according to the invention. It is therefore advantageous to construct the envelope from substances which, upon application, bring about a pleasant feel on the skin, and also to closely match the sensory properties of the envelope and of the filling with one another.

The technical and sensory requirements for the envelope described here extend significantly beyond the usual requirement spectrum for known cosmetic preparations. It is therefore surprising that envelopes according to the invention can be prepared using raw materials which are already known to the person skilled in the art and have already been used in cosmetics.

The following principles for the capsule and its envelope should be observed.

On the one hand, it is possible to solidify lipids which are liquid at room temperature or mixtures of lipids of varying melting ranges which are liquid at room temperature by incorporating water droplets (preparation of a W/O emulsion) in such a way that the resulting W/O emulsion is sufficiently solid even above room temperature to prepare an envelope according to the invention from it. On the other hand, lipids whose melting point is close to the skin temperature of 32° C., i.e. between 30° C. and 40° C., can be used to prepare such an envelope according to the invention. Thirdly, by using suitable waxes, polymeric thickeners and/or gel formers from aqueous and/or lipid systems it is possible to produce a thixotropic preparation with a high yield point which satisfies the requirements of the described envelope. It is obvious to the person skilled in the art that the stated approaches, use of a W/O or O/W emulsion, use of lipids with advantageous melting points, use of thixotropic systems with a suitable yield point can be combined with each other as desired in order to further optimize the properties of the envelope.

By reference to these requirements according to the invention, the person skilled in the art can produce a capsule according to the invention without making an inventive effort. The capsule envelope is thus characterized by the property that it melts upon rubbing and/or distributing on the skin and/or the hair and/or becomes completely or partially liquid due to shear forces and/or dissolves in the filling and/or the skin sebum lipids or as a result of mixing filling and envelope material and is thus no longer perceptible, in particular for the user, as a separate constituent besides the filling.

A plurality of spheres, hollow spheres, dragees or capsules according to the invention can be stored together in a pack made of paper, metal or plastic etc. or individually or in greater numbers via further thin packaging similar to candy paper or separately from one another in a blister pack.

Of particular advantage is the combination of the capsule-shaped preparations with a blister pack which separates the individual dragees or capsules from one another during storage and thus prevents individual capsules from joining together as a result, for example, of inappropriate handling. This can also be achieved by wrapping the individual dragees or capsules with thin films made of paper, metal or plastic. In addition, the capsules can be packaged in tubes made, for example, from polystyrene, or be sealed into films. Besides films made of cellophane, aluminum and paper, it is also possible to use plastic films. In general, PE (degree of polymerization of 3000-4000) serves as material for such packagings. Further options are press-through packs in which, for example, an aluminum foil is sealed onto a plastic film, or shrink packs. The capsules can, for example, also be introduced into folding boxes, cartons, cans or plastic bags.

Individual hollow spheres, dragees or capsules according to the invention can be taken out by simply removing them by hand. It is, however, also possible to facilitate the removal of the capsules according to the invention through a suitable dispenser system. For this purpose, for example, individual hollow spheres, dragees or capsules can be released from the dispense system by operating a simple mechanism. Examples of these are the dispenser systems for candy and other confectionery sold by PEZ International AG under the name "PEZ".

Also advantageous are, however, dispenser systems in which the emulsion capsules are stored in indentations in spirals on a round disk and can be removed individually by a dosing mechanism. Of particular advantage here are embodiments which, from their outer shape, are reminiscent of known cosmetic products, for example, the known NIVEA can, since this reduces the risk of confusion with foods.

During use, individual dragees are removed and rubbed on the skin. As a result of the melting, shearing or dissolving of the solid or semisolid envelope or filling constituents, the product becomes of low viscosity and is readily spreadable and dissolves on or in the skin or the hair. It is obvious to the person skilled in the art that it is perfectly possible for envelope and/or filling to comprise solid constituents whose dissolution during application is neither possible nor desired, namely solids which are already used in conventional cosmetics without the consumer noticing that they are present in solid form. Examples thereof are fillers, sunscreen and color pigments.

The user removes one or more of the capsules and rubs then on the skin as is otherwise customary with skin cream from a can or tube. However, it is advantageous here that a preportioned amount can be used without excess residues and packaging.

The advantage of the capsules according to the invention is the convenient simple single use for inbetween times. Similarly to applying makeup or balm to the lips, a rubbing in of cream or skin care is thus also possible while on the move. Moreover, the consumer can also offer individual capsules to other consumers. Although this is also possible with conventional cosmetic products, the common use of, for example, a cream from one and the same pot amounts psychologically to body contact. An inhibition threshold therefore exists here which is overcome by the present invention.

It is also possible to supply capsules with different properties (e.g. perfume, color, skin feel, sunscreen factor, active ingredients present and combinations of these properties) in one packaging, which is not possible with conventional skin care products.

A further advantage is that the use of the capsules according to the invention is more fun for some users, especially children, than the use of conventional cosmetic products. This can make it easier for parents to protect their children against harmful environmental effects such as, for example, UV radiation.

The person skilled in the art is aware that there is a severe problem in protecting cosmetic products against fungi, yeasts and bacteria which enter the product during use. This happens especially as a result of the product being touched by the consumer during removal. It is obvious that the capsules according to the invention offer a further advantage here since the consumer only touches those capsules which he or she applies immediately. The other capsules remain protected against microbial attack, for which reason it is possible for the contents of preservatives to be lower compared with conventional cosmetic products. Since preservatives are a type of cosmetic raw material which is not very well tolerated, it is thus possible to achieve improved compatibility of the products, which constitutes a further advantage of the present invention.

The capsule-shaped preparations according to the invention can have any desired shapes, but they are preferably spherical with a volume of from 0.1 to 20 ml.

The envelope is constructed from waxes, emulsifiers, polymers or mixtures thereof, optionally additionally comprising water and/or polyols. The envelope has excellent impact stability to withstand mechanical stresses during production and storage, and is thin enough to dissolve rapidly during application. The envelope thickness is preferably 0.001 to 3 mm, in particular thicknesses in the range from 0.01-2 mm.

The use of water is possible without problems in proportions of 50% or 60%.

The envelope is advantageously constructed from waxes such as ceresine, ozokerite, ester waxes, glyceride waxes and/or fatty alcohols, and also solid emulsifiers and mixtures thereof. The waxes may be natural waxes, modified natural waxes, partially synthetic or completely synthetic, depending on their origin.

All of the constituents are chosen so that they ensure the required shape and temperature stability, prevent the filling from drying out as a result of evaporation and rapidly melt upon application, become completely or partially liquid due to shear forces or dissolve in the filling material.

To optimize the elastic properties, polymers can be incorporated into the envelope. Suitable polymers are cellulose ether, polyvinylpyrrolidone, polyacrylates or polymethacrylates, and Eudragit.

The envelope material according to the invention is preferably composed of waxes which are chosen from the group of natural waxes, particularly preferably carnauba wax, candelilla wax, shellac wax, berry wax (Rhus Verniciflura), hydrogenated vegetable oils, such as hydrogenated palm oil or rapeseed oil, beeswax, wool wax (Eucerit)

mono-, di- and triglycerides of higher saturated fatty acids having 10-30 carbon atoms or mixtures thereof, particularly preferably glyceryl tripalmitate (Dynasan 116) and/or glyceryl stearate, Kahl wax 6447 (mixture of fatty acid esters and hydrocarbon polymer), glyceryl tribehenate (Syncrowax HRC)

higher saturated fatty alcohols, particularly preferably those having 14-30 carbon atoms, very particularly preferably stearyl alcohol and/or behenyl alcohol and/or cetyl alcohol synthetic esters, preferably C16-36 alkylhydroxystearoyl stearate, stearyl stearate, cetearyl behenate, C20-40 alkyl stearate, particularly preferably cetyl palmitate, methyl palmitate, methyl stearate, myristyl myristate, myristyl lactate, cetyl lactate, stearyl lactate polymer waxes, preferably polyethylene, polypropylene, polyvinyl ether, polydecene, particularly preferably polyvinyl stearyl ether and hydrogenated polydecene, copolymers, particularly preferably those of ethylene acetate and vinyl acetate, and of polyvinylpyrrolidone and hexadecene, hydrocarbons/paraffin waxes, particularly preferably Cera Microcristallina, paraffin wax, ceresine, ozokerite silicone waxes chemically modified waxes any mixtures of waxes of the groups mentioned.

Envelope compositions which comprise raw materials and/or raw material combinations with the sharpest possible melting points or narrow melting ranges at about 30° C. are advantageous. These may be individual substances, such as, for example, esters of C12-C24 fatty acids with short-chain alcohols (C1-C6), esters of short-chain organic acids (C2-C6) with medium-chain or long-chain fatty alcohols (C12-C24)

esters of pyrrolidonecarboxylic acid with medium-chain or long-chain fatty alcohols (C12-C24)

The specified acids or alcohols can comprise additional groups, such as, for example, alkyl or hydroxy groups (e.g. lactic acid).

Moreover, it is also possible to use eutectic mixtures with a corresponding eutectic temperature, e.g. mixtures of hydrogenated coconut fat with wax esters (C12-C24 fatty acid esterified with C12-C24 fatty alcohol). The selection of suitable eutectic mixtures by investigating the melting behavior of mixtures (for example by means of Differential Scanning Calorimetry DSC) is known to the person skilled in the art.

Waxes which are particularly preferred according to the invention for producing the envelope according to the invention are cetyl palmitate, cetyl ricinoleate, beeswax, hydrogenated cocoglycerides, methyl palmitate, methyl stearate, methyl stearate, ethyl stearate, myristyl lactate, cetyl lactate, stearyl lactate, candelilla wax, carnauba wax, paraffin wax, ceresine, ozokerite, myristyl myristate, tripalmitin, tribehenin, glyceryl palmitostearate, hydrogenated rapeseed oil and C15-C40 alkylstearyl stearate.

Within the context of the present disclosure a generic term which is sometimes used for fats, oils, waxes and the like is the expression "lipids", with which the person skilled in the art is entirely familiar. The terms "oil phase" and "lipid phase" are also used synonymously.

For the purposes of the present invention, waxes advantageously have a melting point of from 20 to 90° C., preferably a melting point of from 25 to 80° C. and particularly preferably a melting point of from 30 to 70° C.

In order to reduce the total wax content of the capsules and thus to achieve a more pleasant and balanced feel on the skin, it may be advantageous to incorporate finely dispersed water droplets into the wax envelope, which is used, for example, in the field of color cosmetics and lip care. Lip care sticks solid at room temperature made of such W/O dispersions are described, for example, in the specification DE 10148313. This technology described therein is thus provided by the present invention.

Additionally, other solid substances may also be present in the envelope which are present in solid form at all times (production, storage, use) (e.g. inorganic pigments, lipid thickeners based on Aerosil, hectorite, bentonite or generally minerals) or provide broad melting ranges above 30° C. (natural fats and waxes, such as shea butter or cocobutter, carnauba wax or candelilla wax, hydrogenated fats, such as hydrogenated coconut fat, microcrystalline waxes, ceresine etc.).

The filling can consist of a hydrous medium, for example an emulsion (o/w, w/o, w/o/w), a gel, a microemulsion or a hydrodispersion. The filling material can consist of all substances and preparations known in cosmetics, in particular O/W or W/O/W emulsions in the form of creams or aqueous gels are advantageous.

It is particularly advantageous and thus preferable according to the invention for the envelope to consist of a W/O emulsion and/or waxes and for the filling to consist of O/W emulsions, hydrous compositions, hydrogels and/or hydrocolloids. This selection reduces any possible mixing of envelope and filling constituents.

Envelope and filling can, independently of one another, comprise the customary auxiliaries and additives which are naturally known to the person skilled in the art. However, it is advantageous here that the additives, independently of one another, may be present in the envelope and/or in the filling. For example, dyes can thus be incorporated only into the envelope without changing the filling constituents and nevertheless pleasing aesthetic effects are achieved. The cosmetic preparations according to the invention can therefore comprise, both in the envelope and in the filling, cosmetic auxiliaries as are customarily used in cosmetics, e.g. preservatives, bactericides, deodorizing substances, antiperspirants, insect repellents, vitamins, agents for preventing foaming, dyes, pigments with a coloring effect, flavorings, denaturants, perfumes, thickeners, softening substances, moisturizing and/or humectant substances, antioxidants, UV filter substances, sensory additives, film formers, surfactants, emulsifiers, fats, oils, waxes, active ingredients or other customary constituents of a cosmetic formulation, such as alcohols, polyols, stabilizing polymers, foam stabilizers, electrolytes, organic solvents or silicone derivatives.

Preferred emulsifiers are O/W emulsifiers. O/W emulsifiers can be chosen, for example, from the group of polyethoxylated or polypropoxylated or polyethoxylated and polypropoxylated products, e.g. of:

fatty alcohol ethoxylates ethoxylated wool wax alcohols, polyethylene glycol ethers of the general formula $$R-O-(-CH_2-CH_2-O-)_n-R',$$

fatty acid ethoxylates of the general formula $$R-COO-(-CH_2-CH_2-O-)_n-H,$$

etherified fatty acid ethoxylates of the general formula $$R-COO-(-CH_2-CH_2-O-)_n-R',$$

esterified fatty acid ethoxylates of the general formula $$R-COO-(-CH_2-CH_2-O-)_n-C(O)-R',$$

polyethylene glycol glycerol fatty acid esters ethoxylated sorbitan esters cholesterol ethoxylates
ethoxylated triglycerides
alkyl ether carboxylic acids of the general formula $R-O-(-CH_2-CH_2-O-)_n-CH_2-COOH$ and $n$ is a number from 5 to 30, polyoxyethylene sorbitol fatty acid esters,
alkyl ether sulfates of the general formula $R-O-(-CH_2-CH_2-O-)_n-SO_3-H$ fatty alcohol propoxylates of the general formula $R-O-(-CH_2-CH(CH_3)-O-)_n-H$, polypropylene glycol ethers of the general formula $R-O-(-CH_2-CH(CH_3)-O-)_n-R'$, propoxylated wool wax alcohols,
etherified fatty acid propoxylates $R-COO-(-CH_2-CH(CH_3)-O-)_n-R'$, esterified fatty acid propoxylates of the general formula $R-COO-(-CH_2-CH(CH_3)-O-)_n-C(O)-R'$, fatty acid propoxylates of the general formula $R-COO-(-CH_2-CH(CH_3)-O-)_n-H$, polypropylene glycol glycerol fatty acid esters
propoxylated sorbitan esters
cholesterol propoxylates
propoxylated triglycerides
alkyl ether carboxylic acids of the general formula $R-O-(-CH_2-CH(CH_3)O-)_n-CH_2-COOH$ alkyl ether sulfates and the acids underlying these sulfates of the general formula $R-O-(-CH_2-CH(CH_3)-O-)_n-SO_3-H$ fatty alcohol ethoxylates/propoxylates of the general formula $R-O-X_n-Y_m-H$, polypropylene glycol ethers of the general formula $R-O-X_n-Y_m-R'$, etherified fatty acid propoxylates of the general formula $R-COO-X_n-Y_m-R'$, fatty acid ethoxylates/propoxylates of the general formula $R-COO-X_n-Y_m-H$.

According to the invention, the polyethoxylated or polypropoxylated or polyethoxylated and polypropoxylated O/W emulsifiers used are particularly advantageously chosen from the group of substances with HLB values of 11-18, very particularly advantageously with HLB values of 14.5-15.5, if the O/W emulsifiers have saturated radicals R and R'. If the O/W emulsifiers have unsaturated radicals R and/or R', or if isoalkyl derivatives are present, then the preferred HLB value of such emulsifiers may also be lower or higher.

It is advantageous to choose the fatty alcohol ethoxylates from the group of ethoxylated stearyl alcohols, cetyl alcohols, cetylstearyl alcohols (cetearyl alcohols). In particular, preference is given to:
polyethylene glycol(13) stearyl ether (steareth-13), polyethylene glycol(14) stearyl ether (steareth-14), polyethylene glycol(15) stearyl ether (steareth-15), polyethylene glycol(16) stearyl ether (steareth-16), polyethylene glycol(17) stearyl ether (steareth-17), polyethylene glycol(18) stearyl ether (steareth-18), polyethylene glycol(19) stearyl ether (steareth-19), polyethylene glycol(20) stearyl ether (steareth-20),
polyethylene glycol(12) isostearyl ether (isosteareth-12), polyethylene glycol(13) isostearyl ether (isosteareth-13), polyethylene glycol(14) isostearyl ether (isosteareth-14), polyethylene glycol(15) isostearyl ether (isosteareth-15), polyethylene glycol(16) isostearyl ether (isosteareth-16), polyethylene glycol(17) isostearyl ether (isosteareth-17), polyethylene glycol(18) isostearyl ether (isosteareth-18), polyethylene glycol(19) isostearyl ether (isosteareth-19), polyethylene glycol(20) isostearyl ether (isosteareth-20),
polyethylene glycol(13) cetyl ether (ceteth-13), polyethylene glycol(14) cetyl ether (ceteth-14), polyethylene glycol(15) cetyl ether (ceteth-15), polyethylene glycol(16) cetyl ether (ceteth-16), polyethylene glycol(17) cetyl ether (ceteth-17, polyethylene glycol(18) cetyl ether (ceteth-18), polyethylene glycol(19) cetyl ether (ceteth-19), polyethylene glycol (20) cetyl ether (ceteth-20),
polyethylene glycol(13) isocetyl ether (isoceteth-13), polyethylene glycol(14) isocetyl ether (isoeteth-14), polyethylene glycol(15) isocetyl ether (isoceteth-15), polyethylene glycol(16) isocetyl ether (isoceteth-16), polyethylene glycol(17) isocetyl ether (isoceteth-17), polyethylene glycol (18) isocetyl ether (isoceteth-18), polyethylene glycol(19) isocetyl ether (isoceteth-19), polyethylene glycol(20) isocetyl ether (isoceteth-20),
polyethylene glycol(12) oleyl ether (oleth-12), polyethylene glycol(13) oleyl ether (oleth-13), polyethylene glycol(14) oleyl ether (oleth-14), polyethylene glycol(15) oleyl ether (oleth-15),
polyethylene glycol(12) lauryl ether (laureth-12), polyethylene glycol(12) isolauryl ether (isolaureth-12).
Polyethylene glycol(13) cetylstearyl ether (ceteareth-13), polyethylene glycol(14) cetylstearyl ether (ceteareth-14), polyethylene glycol(15) cetylstearyl ether (ceteareth-15), polyethylene glycol(16) cetylstearyl ether (ceteareth-16), polyethylene glycol(17) cetylstearyl ether (ceteareth-17), polyethylene glycol(18) cetylstearyl ether (ceteareth-18), polyethylene glycol(19) cetylstearyl ether (ceteareth-19), polyethylene glycol(20) cetylstearyl ether (ceteareth-20).

It is also advantageous to choose the fatty acid ethoxylates from the following group: polyethylene glycol(20) stearate, polyethylene glycol(21) stearate, polyethylene glycol(22) stearate, polyethylene glycol(23) stearate, polyethylene glycol(24) stearate, polyethylene glycol(25) stearate,
polyethylene glycol(12) isostearate, polyethylene glycol(13) isostearate, polyethylene glycol(14) isostearate, polyethylene glycol(15) isostearate, polyethylene glycol(16) isostearate, polyethylene glycol(17) isostearate, polyethylene glycol(18) isostearate, polyethylene glycol(19) isostearate, polyethylene glycol(20) isostearate, polyethylene glycol (21) isostearate, polyethylene glycol(22) isostearate, polyethylene glycol(23) isostearate, polyethylene glycol (24) isostearate, polyethylene glycol(25) isostearate,
polyethylene glycol(12) oleate, polyethylene glycol(13) oleate, polyethylene glycol(14) oleate, polyethylene glycol (15) oleate, polyethylene glycol(16) oleate, polyethylene glycol(17) oleate, polyethylene glycol(18) oleate, polyethylene glycol(19) oleate, polyethylene glycol(20) oleate The ethoxylated alkyl ether carboxylic acid or salt thereof which can be used is advantageously sodium laureth-11 carboxylate.

Sodium laureth 1-4 sulfate can advantageously be used as alkyl ether sulfate.

An ethoxylated cholesterol derivative which can be used advantageously is polyethylene glycol(30) cholesteryl ether. Polyethylene glycol(25) soyasterol has also proven useful.

Ethoxylated triglycerides which can be used advantageously are polyethylene glycol(60) evening primrose glycerides.

It is also of advantage to choose the polyethylene glycol glycerol fatty acid esters from the group consisting of polyethylene glycol(20) glyceryl laurate, polyethylene glycol(21) glyceryl laurate, polyethylene glycol(22) glyceryl laurate, polyethylene glycol(23) glyceryl laurate, polyethylene glycol (6) glyceryl caprate/caprinate, polyethylene glycol(20) glyceryl oleate, polyethylene glycol(20) glyceryl isostearate, polyethylene glycol(18) glyceryl oleate/cocoate.

It is likewise favorable to choose the sorbitan esters from the group consisting of polyethylene glycol(20) sorbitan monolaurate, polyethylene glycol(20) sorbitan monostearate, polyethylene glycol(20) sorbitan monoisostearate, polyethylene glycol(20) sorbitan monopalmitate, polyethylene glycol(20) sorbitan monooleate.

Particularly preferred O/W emulsifiers are triceteareth-4 phosphate, polyglyceryl-3 methylglucose distearate, polyethylene glycol-40 stearate, glyceryl stearate citrate, ceteareth-20, ceteareth-2, cetyldimethicone copolyol; wool wax alcohol, methylglucose sesquistearate, PEG-PPG block polymers (Pluronics F68/127), cetearyl glucoside, stearic acid.

Advantageous W/O emulsifiers which may be used are: fatty alcohols having 8 to 30 carbon atoms, monoglycerol esters of saturated and/or unsaturated, branched or unbranched alkanecarboxylic acids with a chain length of from 8 to 24, in particular 12 to 20, carbon atoms, diglycerol esters of saturated and/or unsaturated, branched or unbranched alkanecarboxylic acids with a chain length of from 8 to 24, in particular 12 to 20, carbon atoms, monoglycerol ethers of saturated and/or unsaturated, branched or unbranched alcohols with a chain length of from 8 to 24, in particular 12 to 20, carbon atoms, diglycerol ethers of saturated and/or unsaturated, branched or unbranched alcohols with a chain length of from 8 to 24, in particular 12 to 20, carbon atoms, polypropylene glycol esters of saturated and/or unsaturated, branched or unbranched alkanecarboxylic acids with a chain length of from 8 to 24, in particular 12 to 20, carbon atoms, polyglyceryl esters of saturated and/or unsaturated, branched or unbranched alkanecarboxylic acids with a chain length of from 8 to 24, in particular 12 to 20, carbon atoms, sorbitan esters of saturated and/or unsaturated, branched or unbranched alkanecarboxylic acids with a chain length of from 8 to 24, in particular 12 to 20, carbon atoms lanolin alcohol.

Preferred W/O emulsifiers are branched or unbranched saturated or unsaturated fatty acids having 12 to 26 carbon atoms, polyglyceryl-3 diisostearate, polyglyceryl-4 isostearate, polyglyceryl-2 dipolyhydroxystearate, cetyl PEG/PPG-10-1 dimethicone, PEG-30 dipolyhydroxystearate, PEG-40 sorbitan perisostearate, cetyldimethicone copolyol, PEG-7 hydrogenated castor oil, PEG 45/dodecyl glycol copolymer, PEG 22/dodecyl glycol copolymer, pentaerythritol isostearate, isostearyldiglyceryl succinate, sorbitan isostearate, polyglyceryl-2 sesquiisostearate, glyceryl isostearate, sorbitan stearate, glyceryl stearate, PEG-25 hydrogenated castor oil, PEG40 sorbitan peroleate, sorbitan oleate, PEG40 sorbitan perisostearate, polyglyceryl-3 oleate, polyglyceryl-2 sesquioleate and polyglyceryl-4 isostearate.

Particularly preferred W/O emulsifiers are polyethylene glycol-45/dodecyl glycol copolymer, polyglyceryl-3 diisostearate, PEG-30 dipolyhydroxystearate, sorbitan isostearate, sorbitan stearate, glyceryl isostearate, glyceryl stearate and sorbitan oleate.

It is also possible to dispense with the lowering of the interfacial energy through emulsifiers or surfactants and instead to stabilize the interface by adding particles which are insoluble in both phases. For this purpose it is possible to use natural or synthetic polymers (polyethylene, nylon, starch and its derivatives) or inorganic particles ($TiO_2$, $Al_2O_3$, $BaSO_4$, BN, silicates, alumosilicates).

The oil phase of the formulations according to the invention is advantageously chosen from the group of polar oils, for example from the group of lecithins and of fatty acid triglycerides, namely the triglycerol esters of saturated and/or unsaturated, branched and/or unbranched alkanecarboxylic acids with a chain length of from 8 to 24, in particular 12 to 18, carbon atoms. The fatty acid triglycerides can, for example, be chosen advantageously from the group of synthetic, semisynthetic and natural oils, such as, for example, cocoglyceride, olive oil, sunflower oil, soybean oil, peanut oil, rapeseed oil, almond oil, palm oil, coconut oil, castor oil, wheatgerm oil, grapeseed oil, thistle oil, evening primrose oil, macadamia nut oil and the like.

For the purpose of the present invention, further advantageous polar oil components can also be chosen from the group of esters of saturated and/or unsaturated, branched and/or unbranched alkanecarboxylic acids with a chain length of from 3 to 30 carbon atoms and saturated and/or unsaturated, branched and/or unbranched alcohols with a chain length of from 3 to 30 carbon atoms, and from the group of esters of aromatic carboxylic acids and saturated and/or unsaturated, branched and/or unbranched alcohols with a chain length of from 3 to 30 carbon atoms. Such ester oils can then advantageously be chosen from the group consisting of octyl palmitate, octyl cocoate, octyl isostearate, octyl dodecyl myristate, octyldodecanol, cetearyl isononanoate, isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate, and synthetic, semisynthetic and natural mixtures of such esters, such as, for example, jojoba oil.

In addition, the oil phase can be chosen advantageously from the group of dialkyl ethers and dialkyl carbonates, advantageous are, for example, dicaprylyl ether (Cetiol OE) and/or dicaprylyl carbonate, for example that available under the trade name Cetiol CC.

It is also preferred to choose the oil components from the group consisting of isoeicosane, neopentyl glycol diheptanoate, propylene glycol dicaprylate/dicaprate, caprylic/capric/diglyceryl succinate, butylene glycol dicaprylate/dicaprate, $C_{12-13}$-alkyl lactate, di-$C_{12-13}$-alkyl tartrate, triisostearin, dipentaerythritol hexacaprylate/hexacaprate, propylene glycol monoisostearate, tricaprylin, dimethyl isosorbide. It is particularly advantageous if the oil phase of the formulations according to the invention has a content of $C_{12-15}$-alkyl benzoate or consists entirely thereof.

Advantageous oil components are also, for example, butyloctyl salicylate (for example that available under the trade name Hallbrite BHB), hexadecyl benzoate and butyloctyl benzoate and mixtures thereof (Hallstar AB) and/or diethylhexyl naphthalate (Hallbrite TQ or Corapan TQ from H&R).

Any mixtures of such oil and wax components can also be used advantageously for the purposes of the present invention.

In addition, the oil phase can likewise advantageously also comprise nonpolar oils, for example those which are chosen from the group of branched and unbranched hydrocarbons and hydrocarbon waxes, in particular mineral oil, vaseline (petrolatum), paraffin oil, squalane and squalene, polyolefins, hydrogenated polyisobutenes and isohexadecane. Among the polyolefins, polydecenes are the preferred substances.

The oil phase can also advantageously have a content of cyclic or linear silicone oils or consist entirely of such oils, although it is preferred to use an additional content of other oil phase components apart from the silicone oil or the silicone oils.

Silicone oils are high molecular weight synthetic polymeric compounds in which silicon atoms are joined via oxygen atoms in a catylated and/or reticular manner and the remaining valencies of silicon are saturated by hydrocarbon radicals (mostly methyl groups, more rarely ethyl, propyl, phenyl groups etc.). Systematically, the silicone oils are referred to as polyorganosiloxanes. The methyl-substituted polyorganosiloxanes, which constitute the most important compounds of this group in terms of amount and are characterized by the following structural formula

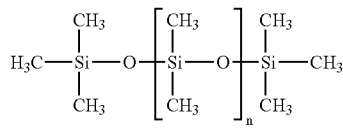

are also referred to as polydimethylsiloxane or Dimethicone (INCI). Dimethicones are available in various chain lengths and with various molecular weights.

Particularly advantageous polyorganosiloxanes for the purposes of the present invention are, for example, dimethylpolysiloxanes [poly(dimethylsiloxane)], which are available, for example, under the trade names Abil 10 to 10 000 from Th. Goldschmidt. Also advantageous are phenylmethylpolysiloxanes (INCI: Phenyl Dimethicone, Phenyl Trimethicone), cyclic silicones (octamethylcyclotetrasiloxane and decamethylcyclopentasiloxane), which are also referred to as cyclomethicones in accordance with INCI, amino-modified silicones (INCI: Amodimethicone) and silicone waxes, e.g. polysiloxanes-polyalkylene copolymers (INCI: Stearyl Dimethicone and Cetyl Dimethicone) and dialkoxydimethylpolysiloxanes (Stearoxy Dimethicone and Behenoxy Stearyl Dimethicone), which are obtainable as various Abil wax grades from Th. Goldschmidt. However, other silicone oils can also be used advantageously for the purposes of the present invention, for example cetyldimethicone, hexamethylcyclotrisiloxane, polydimethylsiloxane, poly(methylphenylsiloxane).

The oil phases described here as being advantageous may be present either in the envelope or in the filling.

It is likewise advantageous to add customary antioxidants to the capsules, the envelope and/or the filling for the purposes of the present invention. According to the invention, favorable antioxidants which may be used are all antioxidants which are customary or suitable for cosmetic and/or dermatological applications.

The antioxidants are advantageously chosen from the group consisting of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, retinoids, such as, for example, retinol, retinal and/or retinoic acid and the respective esters, α-lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl dithiodipropionate, distearylthiodipropionate, thiodipropionic acid and derivatives thereof (esters, ethers, peptides, lipids, nucleotides, nucleosides and salts) and sulfoxime compounds (e.g. buthionin sulfoximines), homocysteine sulfoximine, buthionin sulfones, penta-, hexa-, heptathionin sulfoximine) in very low tolerated doses (e.g. pmol to μmol/kg), also (metal) chelating agents (e.g. α-hydroxy fatty acids, palmitic acid, phytic acid, lactoferrin), α-hydroxyacids (e.g. citric acid, lactic acid, malic acid), humic acid, bile acid, bile extracts, bilirubin, biliverdin, EDTA, IDS, EGTA and derivatives thereof, unsaturated fatty acids and derivatives thereof (e.g. γ-linolenic acid, linoleic acid, oleic acid), folic acid and derivatives thereof, -2-aminopropionic acid diacetic acid, flavonoids, polyphenols, catechins, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), and koniferyl benzoate of benzoin resin, rutinic acid and derivatives thereof, ferulic acid and derivatives thereof, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenemethionine), stilbenes and derivatives thereof (e.g. stilbene oxide, trans-stilbene oxide) and the derivatives suitable according to the invention (salts, esters, ethers, sugars, nucleotides, nucleosides, peptides and lipids) of these specific active ingredients.

The amount of antioxidants (one or more compounds) in the preparations is preferably 0.001 to 30% by weight, particularly preferably 0.05-20% by weight, in particular 0.1-10% by weight, based on the total weight of the preparation.

If vitamin E and/or derivatives thereof are the antioxidant or the antioxidants, it is advantageous to choose their particular concentrations from the range from 0.001-10% by weight, based on the total weight of the formulation.

In addition, UV filter substances can be added to the preparation according to the invention. It is thus preferred to use the preparations according to the invention as sunscreen formulations.

Particularly advantageous UV filter substances which are liquid at room temperature for the purposes of the present invention are homomethyl salicylate (INCI: Homosalate), 2-ethylhexyl 2-cyano-3,3-diphenyl acrylate (INCI: Octocrylene), 2-ethylhexyl 2-hydroxybenzoate (2-ethylhexyl salicylate, octyl salicylate, INCI: Octyl Salicylate) and esters of cinnamic acid, preferably 2-ethylhexyl 4-methoxycinnamate (INCI: Octyl Methoxycinnamate) and isopentyl 4-methoxycinnamate (INCI: Isoamyl p-Methoxycinnamate).

Preferred inorganic pigments are metal oxides and/or other metal compounds which are insoluble or sparingly soluble in water, in particular oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals and mixtures of such oxides, and also the sulfate of barium ($BaSO_4$).

For the purposes of the present invention, the pigments may advantageously also be used in the form of commercially available oily or aqueous predispersions. Dispersion auxiliaries and/or solubilization promoters may advantageously be added to these predispersions.

According to the invention, the pigments can advantageously be surface-treated ("coated"), the aim being to form and/or retain, for example, a hydrophilic, amphiphilic or hydrophobic character. This surface treatment can consist in providing the pigments with a thin hydrophilic and/or hydrophobic inorganic and/or organic layer by methods known per se. For the purposes of the present invention, the various surface coatings can also comprise water.

Inorganic surface coatings for the purposes of the present invention can consist of aluminum oxide ($Al_2O_3$), aluminum hydroxide $Al(OH)_3$, or aluminum oxide hydrate (also: alumina, CAS No.: 1333-84-2), sodium hexametaphosphate $(NaPO_3)_6$, sodium metaphosphate $(NaPO_3)_n$, silicon dioxide ($SiO_2$) (also: silica, CAS No.: 7631-86-9), or iron oxide ($Fe_2O_3$). These inorganic surface coatings can be present on their own, in combination and/or in combination with organic coating materials.

Organic surface coatings for the purposes of the present invention can consist of vegetable or animal aluminum stearate, vegetable or animal stearic acid, lauric acid, dimethylpolysiloxane (also: dimethicone), methylpolysiloxane (methicone), simethicone (a mixture of dimethylpolysiloxane with an average chain length of from 200 to 350 dimethylsiloxane units and silica gel) or alginic acid. These organic surface coatings may be present on their own, in combination and/or in combination with inorganic coating materials.

Zinc oxide particles and predispersions of zinc oxide particles suitable according to the invention are available under the following trade names from the companies listed:

| Trade name | Coating | Manufacturer |
| --- | --- | --- |
| Z-Cote HP1 | 2% dimethicone | BASF |
| Z-Cote | / | BASF |
| ZnO NDM | 5% dimethicone | H&R |

Suitable titanium dioxide particles and predispersions of titanium dioxide particles are available under the following trade names from the companies listed:

| Trade name | Coating | Manufacturer |
| --- | --- | --- |
| MT-100TV | aluminum hydroxide/stearic acid | Tayca Corporation |
| MT-100Z | aluminum hydroxide/stearic acid | Tayca Corporation |
| Eusolex T-2000 | alumina/simethicone | Merck KgaA |
| Titanium dioxide T805 (Uvinul $TiO_2$) | Octyltrimethylsilane | Degussa |

Advantageous UV-A filter substances for the purposes of the present invention are dibenzoylmethane derivatives, in particular 4-(tert-butyl)-4'-methoxydibenzoylmethane (CAS No. 70356-09-1), which is sold by Givaudan under the name Parsol® 1789 and by Merck under the trade name Eusolex® 9020.

Likewise suitable UV-A filter substances are hydroxybenzophenones. These are characterized by the following structural formula:

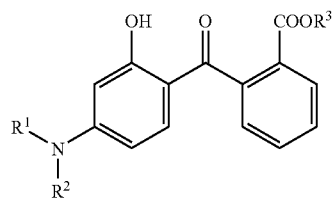

in which
R[1] and R[2], independently of one another, are hydrogen, $C_1$-$C_{20}$-alkyl, $C_3$-$C_{10}$-cycloalkyl or $C_3$-$C_{10}$-cycloalkenyl, where the substituents R[1] and R[2], together with the nitrogen atom to which they are bonded, can form a 5- or 6-membered ring and
R[3] is a $C_1$-$C_{20}$-alkyl radical.

A particularly advantageous hydroxybenzophenone for the purposes of the present invention is hexyl 2-(4'-diethylamino-2'-hydroxybenzoyl)benzoate (also: aminobenzophenone), which is characterized by the following structure:

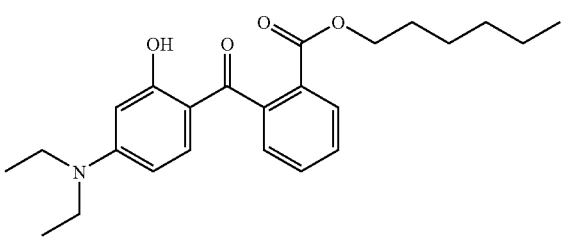 [SMILES: CCCCCCOC(=O)c1ccccc1C(=O)c1ccc(N(CC)CC)cc1O]

and is available under the Uvinul A Plus from BASF.

The total amount of one or more hydroxybenzophenones in the finished cosmetic or dermatological preparations is advantageously chosen from the range 0.01% by weight to 20% by weight, preferably from 0.1 to 10% by weight, in each case based on the total weight of the preparations.

Advantageous further UV filter substances for the purposes of the present invention are sulfonated, water-soluble UV filters, such as, for example phenylene-1,4-bis(2-benzimidazyl)-3,3'-5,5'-tetrasulfonic acid and its salts, particularly the corresponding sodium, potassium or triethanolammonium salts, in particular the phenylene-1,4-bis(2-benzimidazyl)-3,3'-5,5'-tetrasulfonic acid bis-sodium salt with the INCI name Bisimidazylate (CAS No.: 180898-37-7), which is available, for example, under the trade name Neo Heliopan AP;

salts of 2-phenylbenzimidazole-5-sulfonic acid, such as its sodium, potassium or its triethanolammonium salt and the sulfonic acid itself with the INCI name Phenylbenzimidazole Sulfonic Acid (CAS No. 27503-81-7), which is available, for example, under the trade name Eusolex 232 or under Neo Heliopan Hydro from;

1,4-di(2-oxo-10-sulfo-3-bornylidenemethyl)benzene (also: 3,3'-(1,4-phenylenedimethylene)bis(7,7-dimethyl-2-oxobicyclo[2.2.1]hept-1-ylmethanesulfonic acid) and salts thereof (particularly the corresponding 10-sulfato compounds, in particular the corresponding sodium, potassium or triethanolammonium salt), which is also referred to as benzene-1,4-di(2-oxo-3-bornylidenemethyl-10-sulfonic acid). Benzene-1,4-di(2-oxo-3-bornylidenemethyl-10-sulfonic acid) has the INCI name Terephtalidene Dicamphor Sulfonic Acid (CAS No.: 90457-82-2) and is available, for example, under the trade name Mexoryl SX;

sulfonic acid derivatives of 3-benzylidenecamphor, such as, for example, 4-(2-oxo-3-bornylidenemethyl)benzenesulfonic acid, 2-methyl-5-(2-oxo-3-bornylidenemethyl)sulfonic acid and salts thereof.

Advantageous UV filter substances for the purposes of the present invention are also so-called broadband filters, i.e. filter substances which absorb both UV-A and UV-B radiation.

Advantageous broadband filters or UV-B filter substances are, for example, triazine derivatives, such as, for example, 2,4-bis{[4-(2-ethylhexyloxy)-2-hydroxy]phenyl}-6-(4-methoxyphenyl)-1,3,5-triazine (INCI: Aniso Triazine), which is available under the trade name Tinosorb® S;

diethylhexylbutylamidotriazone (INCI: Diethylhexylbutamidotriazone), which is available under the trade name UVASORB HEB;

tris(2-ethylhexyl) 4,4',4"-(1,3,5-triazine-2,4,6-triyltriimino)trisbenzoate, also: 2,4,6-tris[anilino(p-carbo-2'-ethyl-1'-hexyloxy)]-1,3,5-triazine (INCI: Ethylhexyl Triazone), which is sold under the trade name UVINUL® T150.

An advantageous broadband filter for the purposes of the present invention is also 2,2'-methylenebis(6-(2H-benzotriazol-2-yl)-4-(1,1,3,3-tetramethylbutyl)-phenol), which is available under the trade name Tinosorb® M.

An advantageous broadband filter for the purposes of the present invention is also 2-(2H-benzotriazol-2-yl)-4-methyl-6-[2-methyl-3-[1,3,3,3-tetramethyl-1-[(trimethylsilyl)oxy] disiloxanyl]propyl]phenol (CAS No.: 155633-54-8) with the INCI name Drometrizole Trisiloxane, which is available under the trade name Mexoryl® XL.

The further UV filter substances may be oil-soluble or water-soluble.

Advantageous oil-soluble UV-B and/or broadband filter substances for the purposes of the present invention are, for example:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino)benzoate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone and UV filters bound to polymers.

3-(4-(2,2-bisethoxycarbonylvinyl)phenoxy)propenyl) methoxysiloxane/dimethylsiloxane copolymer, which is available, for example, under the trade name Parsol® SLX.

Advantageous water-soluble filter substances are, for example: sulfonic acid derivatives of 3-benzylidenecamphor, such as, for example, 4-(2-oxo-3-bornylidenemethyl)benzenesulfonic acid, 2-methyl-5-(2-oxo-3-bornylidenemethyl) sulfonic acid and salts thereof.

A further photoprotective filter substance to be used advantageously according to the invention is ethylhexyl 2-cyano-3,3-diphenylacrylate (Octocrylene), which is available under the name Uvinul® N 539.

Particularly advantageous preparations for the purposes of the present invention which are characterized by high or very high UV-A and/or UV-B protection comprise, besides the filter substance(s) according to the invention, preferably also further UV-A and/or broadband filters, in particular dibenzoylmethane derivatives [for example 4-(tert-butyl)-4'-methoxy-dibenzoylmethane], phenylene-1,4-bis(2-benzimidazyl)-3,3'-5,5'-tetrasulfonic acid and/or its salts, 1,4-di(2-oxo-10-sulfo-3-bornylidenemethyl)benzene and/or salts thereof and/or 2,4-bis{[4-(2-ethylhexyloxy)-2-hydroxy]phenyl}-6-(4-methoxyphenyl)-1,3,5-triazine, in each case individually or in any combinations with one another.

The list of specified UV filters which can be used for the purposes of the present invention is not of course intended to be limiting.

Advantageously, the preparations according to the invention comprise the substances which absorb UV radiation in the UV-A and/or UV-B region in a total amount of from, for example, 0.1% by weight to 30% by weight, preferably 0.5 to 20% by weight, in particular 1.0 to 15.0% by weight, in each case based on the total weight of the preparations, in order to make available cosmetic preparations which protect the hair and/or the skin from the entire range of ultraviolet radiation. They can also serve as sunscreens for the hair.

Preparations according to the invention particularly advantageously comprise one or more hydrocolloids. These hydrocolloids may be chosen advantageously from the group of gums, polysaccharides, cellulose derivatives, sheet silicates, polyacrylates and/or other polymers.

These hydrocolloids can advantageously be chosen from the above-mentioned group.

The gums include plant or tree saps which harden in the air and form resins or extracts of aquatic plants. From this group, for the purposes of the present invention, it is advantageous to choose, for example, gum arabic, carob seed flour, tragacanth, karaya, guar gum, pectin, gellan gum, carrageen, agar, algins, chondrus, xanthan gum.

Also advantageous is the use of derivatized gums, such as, for example, hydroxypropyl guar (Jaguar® HP 8).

The polysaccharides and polysaccharide derivatives include, for example, hyaluronic acid, chitin and chitosan, chondroitin sulfates, starch and starch derivatives.

The cellulose derivatives include, for example, methylcellulose, carboxymethylcellulose, Hydroxyethylcellulose, hydroxypropylmethylcellulose.

The sheet silicates include naturally occurring and synthetic clay earths, such as, for example, montmorillonite, bentonite, hectorite, laponite, magnesium aluminum silicates, such as Veegum®. These can be used as they are or in modified form, such as, for example, stearylalkonium hectorite.

In addition, silica gels can also be used advantageously.

Also advantageous are taurates, e.g. ammonium acryloyidimethyltaurate/VP copolymer.

The polyacrylates include, for example, Carbopol grades from Goodrich (Carbopol 980, 981, 1382, 5984, 2984, ETD 2001, ETD 2020, ETD 2050, Ultrez-10 or Pemulen TR1 & TR2).

The polymers include, for example, polyacrylamides (Seppigel 305), polyvinyl alcohols, PVP, PVP/VA copolymers, polyglycols.

The water phase of the preparations according to the present invention can advantageously comprise customary cosmetic auxiliaries, such as, for example, alcohols, in particular those of low carbon number, preferably ethanol and/or isopropanol, diols or polyols of low carbon number, and ethers thereof, preferably propylene glycol, glycerol, butylene glycol, ethylene glycol, ethylene glycol monoethyl or monobutyl ether, propylene glycol monomethyl, monoethyl or monobutyl ether, diethylene glycol monomethyl or monoethyl ether, ethylhexyloglycerol, methylpropanediol and analogous products, polymers, foam stabilizers, electrolytes, such as, for example, sodium chloride or magnesium sulfate, and in particular one or more thickeners, which can be chosen advantageously from the group consisting of silicon dioxide, alumosilicates, polysaccharides and derivatives thereof, e.g. hyaluronic acid, xanthan gum, hydroxypropylmethylcellulose, particularly advantageously from the group of polyacrylates, preferably a polyacrylate from the group of so-called Carbopols [from Noveon, formerly Goodrich], for example Carbopol grades 980, 981, 1382, 2984, 5984, ETD 2020, ETD 2050, Ultrez 10, in each case individually or in combination.

In addition, the preparations according to the present invention may advantageously also comprise self-tanning substances, such as, for example, dihydroxyacetone and/or melanine derivatives, in concentrations of from 1% by weight up to 10% by weight, based on the total weight of the preparation.

In addition, the preparations according to the present invention can advantageously also comprise repellents for protecting against flies, ticks and spiders and the like. Of advantage are, for example, N,N-diethyl-3-methylbenzamide (trade name: Metadelphene, "DEET"), dimethyl phthalate (trade name: Palatinol M, DMP), and in particular ethyl 3-(N-n-butyl-N-acetylamino)propionate (available under the trade name Insect Repellent®3535). The repellents can either be used individually or in combination.

Humectants and/or skin-moisturizing substances are the terms used to refer to substances or mixtures of substances which impart to cosmetic or dermatological preparations the property, following application and/or distribution on the surface of the skin, of reducing the release of moisture by the horny later (also termed transepidermal water loss (TEWL)) and/or of positively influencing hydration of the horny layer. Advantageous moisturizers for the purposes of the present invention are, for example, glycerol, lactic acid and/or lactates, in particular sodium lactate, butylene glycol, propylene glycol, panthenol, fucogel, glycine soya, ethylhexyloxyglycerol, pyrrolidonecarboxylic acid and its derivatives, and urea. In addition, it is particularly advantageous to use polymeric moisturizers from the group of water-soluble and/or water-swellable and/or water-gellable polysaccharides. In particular, hyaluronic acid, chitosan and/or a fucose-rich polysaccharide which is deposited in the Chemical Abstracts under the registry number 178463-23-5 and is available, for example, under the name Fucogel® 1000, for example, are advantageous. Moisturizers can advantageously also be used as antiwrinkle active ingredients for the prophylaxis and treatment of cosmetic or dermatological changes in the skin, as arise, for example, during skin aging.

The cosmetic or dermatological preparations according to the invention can also advantageously, although not necessarily, comprise fillers which, for example, further improve the sensory and cosmetic properties of the formulations and, for example, bring about or enhance a velvety or silky feel on the skin. Advantageous fillers for the purposes of the present invention are starch and starch derivatives (such as, for example, tapioca starch, distarch phosphate, aluminum or sodium starch octenylsuccinate and the like), pigments which have neither primarily UV filter effect nor coloring effect (such as, for example, boron nitride etc.) and/or Aerosils® (CAS No. 7631-86-9).

Besides the above-described use of the capsules as sunscreen, skin care and lip care, self-tanning or insect repellent, where ingredients relating to this can be chosen individually, the capsule according to the invention can also be used as a cleansing capsule.

The filling then comprises surfactants or washing-active substances which are released on the skin during rubbing. The incorporation as filling constituent takes place here without any complications.

One problem of hand or face cleansing was that the amount of washing composition was difficult to dose. By virtue of the surfactant-containing capsules the user is given the option of always using the same amounts of washing composition. As a result of the fact that the capsules do not leave behind any residues during use, no additional packaging is produced.

Of advantage particularly when providing the capsules containing surfactants is the combination of the washing-active substances in the filling with the wax in the envelope. In this way, upon dissolution of the capsules during rubbing or under warm water, a formulation is obtained which foams and, as a result of the wax content, is able to also remove water-resistant residues, such as, for example, make-up.

On trips, the face and skin can thus be cleansed as and when required without costly cleansing compositions having to be taken along.

Surfactants are amphiphilic substances which can dissolve organic, nonpolar substances in water. As a result of their specific molecular structure with at least one hydrophilic molecular moiety and one hydrophobic molecular moiety, they bring about a reduction in the surface tension of the water, wetting of the skin, easier soil removal and dissolution, easy rinsing and—if desired—foam regulation.

The hydrophilic moieties of a surfactant molecule are mostly polar functional groups, for example $-COO^-$, $-OSO_3^{2-}$, $-SO_3^-$, while the hydrophobic moieties generally constitute nonpolar hydrocarbon radicals. Surfactants are generally classified according to the type and charge of the hydrophilic molecular moiety. Here, four groups can be differentiated:

anionic surfactants,
cationic surfactants,
amphoteric surfactants and
nonionic surfactants.

As functional groups, anionic surfactants generally have carboxylate, sulfate or sulfonate groups. In aqueous solution, they form negatively charged organic ions in an acidic or neutral medium. Cationic surfactants are virtually exclusively characterized by the presence of a quaternary ammonium group. In aqueous solution, they form positively charged organic ions in an acidic or neutral medium. Amphoteric surfactants contain both anionic and cationic groups and, accordingly, behave like anionic or cationic surfactants in aqueous solution depending on the pH. In a strongly acidic medium, they have a positive charge and in an alkaline medium they have a negative charge. By contrast, in the neutral pH range, they are zwitterionic, as the example below is to illustrate:

$$RNH_2^+CH_2CH_2COOH\ X^- \text{ (at pH=2) } X^-=\text{any anion,}$$
e.g. $Cl^-$ $$RNH_2^+CH_2CH_2COO^- \text{ (at pH=7)}$$

$$RNHCH_2CH_2COO^-\ B^+ \text{ (at pH=12) } B^+=\text{any cation,}$$
e.g. $Na^+$ Typical nonionic surfactants are polyether chains. Nonionic surfactants do not form ions in an aqueous medium.

A. Anionic Surfactants

Anionic surfactants to be used advantageously are acyl-lamino acids (and salts thereof), such as 1. acyl glutamates, for example sodium acyl glutamate, di-TEA palmitoyl aspartate and sodium caprylic/capric glutamate, 2. acyl peptides, for example palmitoyl-hydrolyzed milk protein, sodium cocoyl-hydrolyzed soya protein and sodium/potassium cocoyl-hydrolyzed collagen,
3. sarcosinates, for example myristoyl sarcosine, TEA lauroyl sarcosinate, sodium lauryl sarcosinate and sodium cocoyl sarcosinate,
4. taurates, for example sodium lauroyl taurates and sodium methyl cocoyl taurates,
5. acyl lactylates, lauroyl lactate, caproyl lactylate
6. alaninates carboxylic acids and derivatives, such as
1. carboxylic acids, for example lauric acid, aluminum stearate, magnesium alkanolate and zinc undecylenate,
2. ester carboxylic acids, for example calcium stearoyl lactylate, laureth-6 citrate and sodium PEG4 lauramide carboxylate,
3. ether carboxylic acids, for example sodium laureth-13 carboxylate and sodium PEG-6 cocamide carboxylate, phosphoric esters and salts, such as, for example, DEA-oleth-10 phosphate and dilaureth-4 phosphate, sulfonic acids and salts, such as
1. acyl isethionates, e.g. sodium/ammonium cocoyl isethionate,
2. alkylarylsulfonates,
3. alkylsulfonates, for example sodium cocomonoglyceride sulfate, sodium $C_{12-14}$ olefinsulfonate, sodium lauryl sulfoacetate and magnesium PEG-3 cocamide sulfate,
4. sulfosuccinates, for example dioctyl sodium sulfosuccinate, disodium laureth sulfosuccinate, disodium lauryl sulfosuccinate, disodium undecylenamido-MEA sulfosuccinate and PEG-5 lauryl citrate sulfosuccinate.

and
sulfuric esters, such as
1. alkyl ether sulfate, for example sodium, ammonium, magnesium, MIPA, TIPA laureth sulfate, sodium myreth sulfate and sodium $C_{12-13}$-pareth sulfate,
2. alkyl sulfates, for example sodium, ammonium and TEA lauryl sulfate.

B. Cationic Surfactants
Cationic surfactants to be used advantageously are
1. alkylamines,
2. alkylimidazoles,
3. ethoxylated amines and
4. quaternary surfactants.
5. ester quats Quaternary surfactants contain at least one N atom which is covalently bonded to 4 alkyl and/or aryl groups. Irrespective of the pH, this leads to a positive charge. Advantageous quaternary surfactants are alkylbetain, alkylamidopropylbetain and alkylamidopropylhydroxysulfain. For the purposes of the present invention, cationic surfactants may also preferably be chosen from the group of quaternary ammonium compounds, in particular benzyltrialkylammonium chlorides or bromides, such as, for example, benzyldimethylstearylammonium chloride, also alkyltrialkylammonium salts, for example cetyltrimethylammonium chloride or bromide, alkyldimethylhydroxyethylammonium chlorides or bromides, dialkyldimethylammonium chlorides or bromides, alkylamide ethyltrimethylammonium ether sulfates, alkylpyridinium salts, for example lauryl- or cetylpyrimidinium chloride, imidazoline derivatives and compounds with cationic character, such as amine oxides, for example alkyldimethylamine oxides or alkylaminoethyldimethylamine oxides. In particular, cetyl-trimethylammonium salts are to be used advantageously.

C. Amphoteric Surfactants
Amphoteric surfactants to be used advantageously are
1. acyl-/dialkylethylenediamine, for example sodium acylamphoacetate, disodium acylamphodipropionate, disodium alkylamphodiacetate, sodium acylamphohydroxypropylsulfonate, disodium acylamphodiacetate and sodium acylamphopropionate,
2. N-alkylamino acids, for example aminopropylalkylglutamide, alkylaminopropionic acid, sodium alkylamidodipropionate and lauroamphocarboxyglycinate.

D. Nonionic Surfactants
Nonionic surfactants to be used advantageously are
1. alcohols,
2. alkanolamides, such as cocoamides MEA/DEA/MIPA,
3. amine oxides, such as cocoamidopropylamine oxide,
4. esters which are formed by esterification of carboxylic acids with ethylene oxide, glycerol, sorbitan or other alcohols,
5. ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers and alkyl polyglycosides, such as lauryl glucoside, decyl glycoside and cocoglycoside.
6. Sucrose esters, sucrose ethers
7. Polyglycerol esters, diglycerol esters, monoglycerol esters
8. methylglucose ester, esters of hydroxy acids Also advantageous is the use of a combination of anionic and/or amphoteric surfactants with one or more nonionic surfactants.

According to the invention, for use, the capsule-shaped preparations are applied to the skin and/or the hair in the manner customary for cosmetics and rubbed and/or distributed.

The advantage essential to the invention is the provision for the first time of individual handleable cosmetic preparations in capsule form which offer the consumer simplified removal, improved hygiene when sharing the product with others, and a new application form.

The cosmetic and/or dermatological preparations according to the invention can be composed like customary cosmetic and/or dermatological preparations and serve for cosmetic and/or dermatological photoprotection, for changing or influencing certain skin conditions, also for the treatment, care and cleansing of the skin and/or of the hair and as a make-up product in decorative cosmetics.

Accordingly, cosmetic and/or topical dermatological compositions for the purposes of the present invention can, depending on their formulation, be used, for example, as skin care product, skin protection product, cleansing product, sunscreen product, hair treatment, body cleansing product, for day or night care, the care of certain areas of skin, such as hands, face, feet etc.

The use of the capsule-shaped cosmetic preparations according to the invention for the prophylaxis and treatment of the symptoms of aging skin, for preventing and reducing the formation and spread of wrinkles and lines, and for the treatment and care of aged skin is also in accordance with the invention. Thus, an individual capsule comprising ubiquinone, ubiquinol, retinol and derivatives, dehydroepiandrosterone (DHEA), isoflavonoids (in particular genistein, daidzein), creatin, phytoestrogens, estrogen, estradiol and derivatives, niacinamide, polyphenols (AGR) or another substance effective against lines can advantageously be applied and distributed on the facial skin.

In addition, the use of the capsule-shaped cosmetic preparations according to the invention for the prophylaxis and treatment of the symptoms of dry skin is preferred. Suitable active ingredients for this use purpose are: natural oils (sunflower oil, evening primrose seed oil, jojoba oil, macadamia oil, castor oil), ceramides, in particular ceramide I, III and VI, cholesterol, phytosterols, fatty acids with a chain length of C16-26, carnitine and its derivatives, urea, polyols such as glycerol, butylene glycol, propylene glycol and dipropylene glycol, pseudoceramides; electrolytes, such as sodium chloride and taurine, fatty alcohols, and waxes.

Furthermore, the use of the capsule-shaped cosmetic preparations according to the invention for the prophylaxis and treatment of the symptoms of sensitive and/or inflamed skin is advantageous. Preferred active ingredients for this intended use are: ingredients of milk thistle, in particular silymarin, hamamelis extract, camomile extract, ingredients of the liquorice plant (glycerrhicinic acid, licochalcones A & B), allantoin, acetylsalicylic acid, diclofenac, pentacyclic triterpenes (sericosides, urolic acid) and panthenol.

Furthermore, the use of the capsule-shaped cosmetic preparations according to the invention for the prophylaxis and treatment of the symptoms of incorrectly pigmented skin is advantageous. Preferred active ingredient for this intended use are: tyrosinase inhibitors, hydroquinone derivatives, dioic acid, lipoic acid and its derivatives, and kojic acid.

It is in some cases possible and advantageous to use the compositions according to the invention as a base for pharmaceutical formulations. In addition, the use of the capsule-shaped cosmetic preparations according to the invention for the prophylaxis and treatment of the symptoms of diseased skin is preferred. Relevant but nonexclusive diseased skin conditions are psoriasis, acne, neurodermitis and other atopic disorders, such as atopic dermatitis, skin cancer, herpes, mycoses, ichthyosis, pityriasis, seborrhea, pellagra, contact eczema and allergies. Suitable active ingredients for such intended uses are antibiotics, such as fusidic acid, erythromycin, sulfadiazine, clindamycin, tetracyclines, tyrothricin aminoglycosides, bacitracin, chloramphenicol, virostatics (e.g. acyclovir, idoxuridin, penciclovir), antimycotics (e.g. nystatin, amphotericin, clotrimazole, econazole, keto-conazole, naftifin, terbinafin), allethrin, cytostatics (5-fluorouracil), antiphlogistics (hydrocortisone, betamethasone; prednisolone, triamcinolone acetonide, dexamethasone, diclofenac, bufexamac), immunosuppressants (cyclosporine A, interferon-beta), antipsoriatics (dithranol, psoralene, tazarotene), acne agents (retinoic acid, isotretinoin, benzoyl peroxide, adapalene); capsaicin, azelaic acid, keratolytics (salicylic acid, lactic acid), antihistamines (azelastin, levocabastin, disodium cromoglycine); antipsoriatics (dithranol, calcitriol, psoralene) and vitamins (particularly the A, B and C vitamins).

One possible use which is particularly advantageous according to the invention is to supply capsules with different intended uses in one pack, for example those for day care and night care, those with different colors, fragrances, different strength sunscreen factors or different active ingredients. With such a use, it is particularly advantageous to make the capsules with a different composition distinguishable for the user through different shaping and/or coloring.

Last but not least, the use of the cosmetic and/or dermatological preparations according to the invention for the prophylaxis, treatment and cleansing of greasy skin, and also for the prophylaxis and treatment of unblemished skin and of cellulite is in accordance with the invention.

To prepare the capsule-shaped preparations according to the invention, the envelope and the filling are firstly produced separately from one another. The covering of the filling with the enveloping material can take place in various ways, irrespective of the composition of the filling material or of the envelope.

For example, the filling material can be frozen and then be dipped into molten enveloping material, as a result of which a solid, closed envelope forms on the filling material.

However, it is also possible to cast hollow spheres from molten enveloping material which are possibly filled with filling material through a hole in the wall of the sphere. The hole is then sealed by a plug of enveloping material. It is also possible to firstly cast half hollow spheres, to possibly fill these, position them congruently and finally melt them together by thermal treatment. Moreover, two such half spheres can be produced where one or both have a hole for subsequent filling, then welded to give a hollow sphere and finally filled through the filling hole, which is then closed as described above. A particularly preferred and inventive method of producing the capsules and the envelope thereof proceeds according to the principle of the frozen-cone or cold-stamp method, as are described, for example, in DE 19852262 or DE 9321186. These methods from food technology have been adapted according to the invention to the preparation of cosmetic preparations.

The frozen-cone method is illustrated in the attached FIG. 1. A defined amount of enveloping mass 3 is firstly poured through a nozzle 2 into a mold 1. By pressing in a chilled shaped body 4 (frozen cone or cold stamp), the introduced enveloping mass is molded and simultaneously cooled so that it does not change or not significantly change its shape until the filling mass 6 is poured through a further nozzle 5. After introducing the filling mass, further enveloping mass 3a is applied through the nozzle 2a. The nozzles 2 and 2a and the masses 3 and 3a may, but do not have to be identical. It is advantageous to choose the masses 3 and 3a to be identical. Finally, the finished emulsion capsule 7 is removed from the mold.

Alternatively, after introducing the filling, two unsealed half capsules can be positioned congruently with respect to one another and their envelopes melted together.

Using this method, the envelope thicknesses can be adjusted variably in the range from 0.001 to 3 mm. Compared with the prior art, capsule preparations with extremely thin walls can thus be produced for the first time.

A further advantage of the method is that the filling to be added does not need to be heated subsequently. This is particularly advantageous if the filling comprises thermally sensitive materials which are decomposed at elevated temperatures, e.g. oxidatively (vitamins A, B, C and E or their derivatives, such as acetates, phosphates or palmitates, provitamin B5) or hydrolytically (acetylcarnitine, parabens). The cold processing of the filling can of course also save energy, which reduces the production costs and is less of an impact on the environment.

In order to be able to provide the capsules according to the invention in a wide variety of shapes, size and thickness of the envelope, the one-shot method, known from the food sector, has likewise proven useful. This method too has been adapted according to the invention for producing the cosmetic capsules according to the invention.

Figure 2:
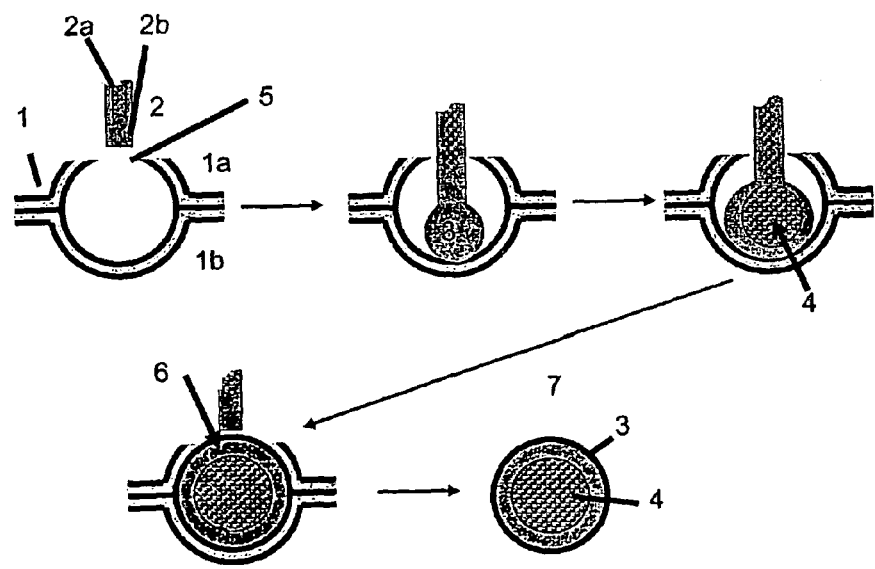
FIG. 2 shows a schematic representation which illustrates another process for making a filled capsule of the present invention.

For this, a mold 1 is formed from an upper half-mold and a lower half-mold (1a and b) (cf. FIG. 2), where the upper half-mold 1a has an opening 5. A twin nozzle 2, in which an inner channel 2a is arranged concentrically in an outer channel 2b, is passed through this into the mold 1. Firstly, some enveloping mass 3 is conveyed through the outer channel into the mold so that a continuous base is formed from envelope mass. Shortly afterward, the delivery of the filling 4 through the inner channel 2a starts. During the delivery of the two masses, the nozzle 2 moves upward out of the mold 1. Finally, the delivery of the filling is again briefly interrupted so that a continuous lid 6 can also form. By subsequently separating the two half-molds 1a and b from one another it is possible to release the finished emulsion capsule 7 from the mold.

Alternatively, the upper half-mold 1a can be dispensed with so that the opening 5 is formed directly by the opening or its open side of the lower half-mold 1b. The masses 3 and 4 are filled directly through the twin nozzle 2 into the lower half-mold 1b, similar to the method as in FIG. 1.

Thus it is possible to produce capsules, but not in sphere form, but only bodies with a planar base surface (e.g. like chocolates praline toffee-fee or Mozart balls known from the food sector). These shapes too are thus also in accordance with the invention.

For the "one-shot"-equivalent method according to the invention, the lowest possible tackiness of the filling mass is required. Tackiness is understood as meaning the property of not immediately tearing off when part of a liquid or semisolid preparation is removed, but of drawing threads between the removed section and the untouched section of the preparation. Thus, for example, molten cheese is extremely tacky, whereas water is not tacky, i.e. does not draw threads. If, then, the filling mass draws threads, then it also does not tear off cleanly when its delivery stops. Due to the threads which are formed, no completely continuous lid made of envelope material can form, as a result of which the emulsion capsule is adversely affected with regard to its mechanical properties (dimensional stability, hardness, elasticity) and other properties (water loss, leakage of the filling mass).

Cosmetic raw materials, such as, for example, polyols (particularly glycerol, propylene glycol, butylene glycol, polyethylene glycol, pentanediols, hexanediols, octanediols) or hydrocolloids (particularly polysaccharides such as starch and starch derivatives, mannans, glucans, xanthan gum, guar gum, gum arabic, and polymers or copolymers of acrylic acid or their esters) can increase the tackiness of the filling and thus make themselves noticeable in a negative way in the production method. As a constituent of the filling, this leads to the drawing of threads while charging the envelope. The envelope can then only be closed with problems. This problem of filling can, surprisingly, be solved by modifying the envelope by adding surface-active substances, preferably W/O emulsifiers, to the envelope. Preferred W/O emulsifiers are branched or unbranched, saturated or unsaturated fatty acids having 12 to 26 carbon atoms, polyglyceryl-3 diisostearate, polyglyceryl-4 isostearate, polyglyceryl-2 dipolyhydroxystearate, cetyl PEG/PPG-10-1 dimethicone, PEG-30 dipolyhydroxystearate, PEG40 sorbitan perisostearate, cetyldimethicone copolyol, PEG-7 hydrogenated castor oil, PEG 45/dodecyl glycol copolymer, PEG 22/dodecyl glycol copolymer, pentaerythrityl isostearate, isostearyl diglyceryl succinate, sorbitan isostearate, glyceryl-2 sesquiisostearate, glyceryl isostearate, sorbitan stearate, glyceryl stearate, PEG-25 hydrogenated castor oil, PEG40 sorbitan peroleate, sorbitan oleate, PEG40 sorbitan perisostearate, polyglyceryl-3 oleate, polyglyceryl-2 sesquioleate and polyglyceryl-4 isostearate. Moreover, it is also possible to use waxes with contents of surface-active substances, primarily those with contents of free fatty acids and/or fatty acid mono- or diglycerides (e.g. bees waxes). They thus make the pouring of fillings which comprise glycerol, hydrocolloids and/or the above-described substances significantly easier. The thread which otherwise forms is severed through the addition of the surface-active substances by the envelope. The addition thus ensures a problem free closure of the envelope. The problem of filling (thread drawing) is solved according to the invention by envelope constituents.

The frozen-cone or cold-stamp method is characterized by its excellent precision and reproducibility in the thickness and uniformity of the envelope. It is particularly well suited to molding very thin envelopes (<1 mm).

The advantage of the one-shot method is its extraordinary flexibility: by adjusting a few of the machine parameters it is possible to produce capsules with envelopes of different thicknesses using identical nozzles, machines and molds. To change the shape of the capsule (for example oval instead of round) the same machine can be used, only the half-molds have to be exchanged.

The molds into which material is poured in both methods can be produced from various materials, particularly preferably thermoplasts, such as polyolefins, vinyl polymers, polyamides, polyesters, polyacetals and polycarbonates. They are advantageously produced as disposable molds (blisters), which can be used for packaging the finished capsules.

Both of the methods according to the invention described above permit an industrial production through machines of the capsule-shaped cosmetic preparations, meaning that the production costs can be reduced and thus also good-value capsule-shaped cosmetics can be supplied.

In addition, the preparation according to the invention has improved sensory properties which are not to be expected with wax-containing preparations from the prior art. Improved spreadability, ability to soak in, consistency, skin smoothing and reduced stickiness have been established. For suitable methods of determining these parameters, reference may be made to the knowledge of the person skilled in the art.

It is particularly surprising that the capsule according to the invention can be used without filling, as a hollow sphere, likewise as independent cosmetic. The substances present for the cosmetic or dermatological purpose are then all located according to the invention in the envelope.

The sizes given, such as, for example, the diameter of the capsules, should be understood as meaning the diameter in the direction of the longitudinal extension of the capsule particles.

The examples below explain the capsule-shaped preparations according to the invention. Unless stated otherwise, the percentages given are based on the total mass of the preparations.

EXAMPLES

A. Examples of the Composition of the Filling (Data in Mass Percent Based on the Total Weight of the Filling)

Examples 1-5

O/W Creams

|  | Example | | | | |
| --- | --- | --- | --- | --- | --- |
|  | 1 | 2 | 3 | 4 | 5 |
| Glyceryl stearate citrate | 2 |  |  |  |  |
| Glyceryl stearate, self-emulsifying |  | 5 | 3 | 1 | 2 |
| PEG-40 stearate |  |  | 1 |  | 1 |
| Stearic acid |  |  |  | 4 |  |
| Myristyl myristate |  | 1 |  |  | 1 |

|  | Example | | | | |
|---|---|---|---|---|---|
|  | 1 | 2 | 3 | 4 | 5 |
| Behenyl alcohol |  |  |  | 1 |  |
| Stearyl alcohol | 2 | 1 |  |  |  |
| Cetearyl alcohol |  |  |  |  | 2 |
| Cetyl alcohol | 1 |  | 3 | 3 |  |
| Hydrogenated cocoglycerides | 2 |  |  |  |  |
| Shea butter |  | 1 |  |  | 2 |
| C12-15 alkyl benzoate |  | 3 | 2 |  | 3 |
| Butylene glycol dicaprylate/dicaprate | 1 |  |  | 1 |  |
| Caprylic/capric triglyceride |  | 1 | 2 | 2 | 2 |
| Ethylhexyl coconut fatty acid ester | 3 |  |  |  | 1 |
| Octyldodecanol |  |  | 1 |  |  |
| Jojoba oil |  |  |  | 1 |  |
| Mineral oil |  | 1 |  |  |  |
| Vaseline | 1 |  | 1 |  | 2 |
| Cyclomethicone | 3 | 2 | 4 | 3 | 5 |
| Dimethicone |  |  | 1 | 1 |  |
| Dicaprylyl ether | 1 | 3 | 2 |  |  |
| Dicaprylyl carbonate |  |  |  | 3 |  |
| TiO$_2$ | 1 |  | 1 |  | 1 |
| Ethylhexyl methoxycinnamate | 5 | 3 | 5 |  | 3 |
| Ethylhexyltriazone |  | 1 |  |  |  |
| Ethylhexyl cyanodiphenyl acrylate (octocrylene) |  |  |  | 5 | 3 |
| Butylmethoxydibenzoylmethane | 1 |  |  |  |  |
| Bisethylhexyloxyphenol methoxyphenyltriazine |  | 1 |  |  |  |
| Ethylhexyl salicylate | 1 |  |  |  |  |
| 2-Hydroxy-4-methoxybenzophenone (oxybenzone) |  |  | 2 | 3 | 2 |
| Phenylbenzimidazole sulfonic acid |  |  |  | 2 |  |
| Ubiquinone (Q10) |  |  | 0.03 |  |  |
| Tocopheryl acetate |  |  | 1 |  | 0.3 |
| Citric acid, sodium salt |  | 0.1 |  |  |  |
| Creatine | 0.5 |  |  |  |  |
| Sodium ascorbyl phosphate |  |  |  |  | 0.1 |
| Phenoxyethanol | 0.3 |  | 0.3 | 0.2 | 0.2 |
| p-Hydroxybenzoic alkyl ester (parabens) | 0.6 | 0.3 | 0.2 | 0.3 | 0.3 |
| Hexamidine diisethionate |  | 0.04 |  |  |  |
| Diazolidinylurea | 0.25 |  | 0.1 | 0.2 | 0.1 |
| 1,3-Dimethylol-5,5-dimethylhydantoin (DMDM hydantoin) |  | 0.2 |  |  |  |
| Iodopropynyl butylcarbamate |  | 0.1 |  |  |  |
| Ethanol (denatured) |  | 2 |  |  |  |
| Xanthan gum |  |  | 0.1 |  |  |
| Polyacrylic acid (carbomer) | 0.05 |  |  |  | 0.1 |
| Ammonium polyacryloyldimethyl taurate | 0.4 |  |  | 0.3 |  |
| Ammonium acryloyldimethyl-taurate/vinylpyrrolidone copolymers |  | 0.5 | 0.3 |  |  |
| Aluminum starch octenylsuccinate |  |  |  |  | 0.5 |
| Glycerol | 10 | 6 | 7 | 7 | 5 |
| Butylene glycol |  | 1 |  | 1 |  |
| Water- and/or oil-soluble dyes | 0.05 |  |  |  |  |
| Fillers/additives (distarch phosphate, SiO$_2$, BHT, talc, aluminum stearate) | 0.1 | 1 | 0.2 | 0.5 | 0.05 |
| Perfume | q.s | q.s | q.s | q.s | q.s |
| Water | ad 100 | ad 100 | ad 100 | ad 100 | ad 100 |

Example 6

Hydrodispersion/Gel Cream

| | |
|---|---|
| Cetyl alcohol | 2 |
| Shea butter | 1 |
| Caprylic/capric triglyceride | 2 |
| Octyldodecanol | 1 |
| Octamethyltetrasiloxane (cyclomethicone) | 5 |
| Dimethylpolysiloxane (dimethicone) | 1 |
| Polydecene | 2 |
| Ethylhexyl methoxycinnamate | 3 |
| Bisethylhexyloxyphenol methoxyphenyltriazine | 0.5 |
| Sodium ascorbyl phosphate | 0.05 |
| Iminodisuccinate | 0.2 |
| Ubiquinone | 0.05 |
| Phenoxyethanol | 0.3 |
| p-Hydroxybenzoic alkyl ester (parabens) | 0.4 |
| Crosslinked alkyl acrylate (alkyl acrylate crosspolymer) | 0.2 |
| Glycerol | 5 |

-continued

| | |
|---|---|
| Perfume | q.s. |
| Water | ad 100 |

B. Examples of the Composition of the Envelope (Data in Mass Percent Based on the Total Weight of the Envelope)

Examples 7-11

Wax Envelope

| | Example | | | | |
|---|---|---|---|---|---|
| | 7 | 8 | 9 | 10 | 11 |
| Myristyl myristate | 20 | | | | 5 |
| Ceresine | 5 | 5 | | | 4 |
| Cera Alba | 15 | | | | |
| Shea butter | 10 | 15 | | | 7.5 |
| Hydrogenated coconut fat | 20 | ad 100 | 10 | | 5 |
| Cera Microcristallina | 5 | | | | 5 |
| Glyceryl stearate citrate | | 20 | | | |
| Octyldodecanol | | | 15 | | 5 |
| Methyl palmitate | ad 100 | | | 25 | |
| Ozokerite | | 20 | | 10 | 5 |
| Hydrogenated polydecene | | | 15 | | |
| Polyethylene | | | 15 | 5 | |
| PEG-45/dodecyl glycol copolymer | | | 2 | | |
| Polyglyceryl-3 diisostearate | | | 3 | | |
| Lanolin alcohol | | | | 1 | 2 |
| Polyglyceryl-3 diisostearate | | | | 1 | |
| PEG-40 sorbitan perisostearate | | | | 3 | |
| Magnesium stearate | | | | | 0.4 |
| Aluminum stearate | | | | | 0.1 |
| Magnesium sulfate | | | 1 | | |
| Sodium chloride | | | | 1 | 1 |
| Preservative | q.s | q.s | q.s | q.s | q.s |
| Perfume | q.s | q.s | q.s | q.s | q.s |
| Water | | | ad 100 | ad 100 | ad 100 |

Examples 12-16

Wax Envelope

| | Example | | | | |
|---|---|---|---|---|---|
| | 12 | 13 | 14 | 15 | 16 |
| Myristyl myristate | | | 13 | | 5 |
| Ceresine | 5 | | | | 2 |
| Cera Alba | | | 10 | | |
| Shea butter | | 10 | | 11 | |
| Hydrogenated coconut fat | | 10 | | | |
| Cera Microcristallina | 5 | 3.5 | | 5 | |
| Octyldodecanol | | 10 | | 5 | 9 |
| Methyl palmitate | 25 | | 5 | 7 | 20 |
| Ozokerite | | 10 | | 5 | |
| Hydrogenated polydecene | | | | 2 | |
| Polyethylene | 5.5 | | | | 4 |
| Polyglyceryl-3 diisostearate | | | | 3 | |
| Lanolin alcohol | 0.6 | | 0.5 | 0.5 | |
| Magnesium stearate | 0.4 | | | 0.5 | |
| Aluminum stearate | 0.01 | | | | |
| Polyglyceryl-3 diisostearate | 2.5 | | | | |
| PEG-30 dipolyhydroxystearate | | 1.5 | | | |
| PEG-7 hydrogenated castor oil | | 0.5 | | | |
| Polyglyceryl-2 dipolyhydroxystearate | | | | 1 | |
| Boron nitride | | | | | 5 |
| Magnesium sulfate | 1 | | 1 | | 1 |
| Sodium chloride | | | | 1 | |
| Preservative | q.s | q.s | q.s | q.s | q.s |
| Perfume | q.s | q.s | q.s | q.s | q.s |
| Water | ad 100 | ad 100 | ad 100 | ad 100 | ad 100 |

Examples 17-21

Wax Envelope

| | Example | | | | |
|---|---|---|---|---|---|
| | 17 | 18 | 19 | 20 | 21 |
| Myristyl myristate | 20 | | | | 5 |
| Cera Alba | 20 | | | | |
| Shea butter | | 20 | | | 7.5 |
| Hydrogenated coconut fat | 20 | ad100 | 10 | | 9 |
| Cera Microcristallina | 5 | | | | 5 |
| Glyceryl stearate citrate | | 20 | | | |
| Methyl palmitate | ad 100 | | | 10 | |
| Cetyl ricinoleate | 10 | | | 15 | 5 |
| Ozokerite | | 20 | | 10 | 5 |
| Hydrogenated polydecene | | | 15 | | |
| Polyethylene | 5 | | 15 | 5 | |
| Glyceryl stearate | | | 2 | | |
| Polyglyceryl-3 diisostearate | | | 3 | | |
| Lanolin alcohol | | | | 1 | 2 |
| Polyglyceryl-3 diisostearate | | | | 1 | |
| Sorbitan stearate | | | | 1 | 3 |
| Magnesium stearate | | | | | 0.4 |
| Aluminum stearate | | | | | 0.1 |
| Magnesium sulfate | | | 1 | | |
| Sodium chloride | | | | 1 | 1 |
| TiO2 | | 2 | | 2 | |
| Ethylhexyl methoxycinnamate | 5 | | 5 | | |
| PVP | | | | 1 | |
| PVP-hexadecene copolymer | | 1 | | | |
| Methylhydroxypropylcellulose | | | 2 | | |
| Ethylcellulose | 2 | | | | 1 |
| Butylmethoxydibenzoylmethane | 1 | | 2 | | |
| Dimethicone copolyol | | | | | |
| Glycerol | | | 10 | 5 | 15 |
| Preservative | q.s | q.s | q.s | q.s | q.s |
| Perfume | q.s | q.s | q.s | q.s | q.s |
| Water | | | ad 100 | ad 100 | ad 100 |

Examples 22-25

Wax Envelope

| | Example | | | |
|---|---|---|---|---|
| | 22 | 23 | 24 | 25 |
| Myristyl myristate | | | 13 | |
| Cera Alba | | | 10 | |

-continued

| | Example | | | |
|---|---|---|---|---|
| | 22 | 23 | 24 | 25 |
| Shea butter | | 10 | | 11 |
| Hydrogenated coconut fat | | 10 | | |
| Cera Microcristallina | 5 | 3.5 | | 5 |
| Octyldodecanol | | 10 | | 5 |
| Methyl palmitate | 30 | | 5 | 7 |
| Ozokerite | | 10 | | 5 |
| Hydrogenated polydecene | | | | 2 |
| Polyethylene | 5.5 | | | |
| Polyglyceryl-3 diisostearate | 2.5 | 3 | | 3 |
| Lanolin alcohol | 0.6 | | 0.5 | 0.5 |
| Magnesium stearate | 0.4 | | | |
| Aluminum stearate | 0.01 | | | |
| Bentonite | | | | 1 |
| Cetearyl alcohol | | 1.5 | | |
| PEG-7 hydrogenated castor oil | | | 0.5 | |
| Polyglyceryl-2 dipoly-hydroxystearate | | | | 1 |
| TiO$_2$ | 1 | | | |
| Ethylhexyl methoxycinnamate | 3 | | 2 | |
| PVP | | | | |
| PVP-hexadecene copolymer | 1 | | | |
| Methylhydroxypropylcellulose | | 1 | | |
| Ethylcellulose | | 1 | 1 | 1 |
| Butylmethoxydibenzoylmethane | 2 | | 1 | |
| Dimethicone copolyol | | | | 1 |
| Glycerol | 5 | 3 | | 1 |
| Magnesium sulfate | 1 | | 1 | |
| Sodium chloride | | | | 1 |
| Preservative | q.s. | q.s. | q.s. | q.s. |
| Perfume | q.s. | q.s. | q.s. | q.s. |
| Water | ad 100 | ad 100 | ad 100 | ad 100 |

Examples of particularly preferred formulation examples of W/O envelope masses (data in % by weight based on the particular mass)

| | Example 26 |
|---|---|
| Methyl palmitate | 15.0 |
| Microcrystalline wax | 10.0 |
| Polyethylene | 5.0 |
| PEG-40 sorbitan perisostearate | 2.0 |
| Eucerit | 0.5 |
| Polyglyceryl-3 diisostearate | 1.0 |
| Glycerol | 5.0 |
| MgSO$_4$ | 0.2 |
| Iodopropynyl butylcarbamate | q.s. |
| Parabens | q.s. |
| Perfume | q.s. |
| Water | ad 100 |

| | Example 27 |
|---|---|
| Methyl stearate | 20.0 |
| Microcrystalline wax | 8.0 |
| Carnauba wax | 7.0 |
| C12-C15 alkyl benzoate | 3.0 |
| Polyglyceryl-2 dipolyhydroxystearate | 2.0 |
| Polyglyceryl-3 diisostearate | 1.0 |
| Glycerol | 6.0 |
| MgSO$_4$ | 0.3 |
| Hydrophobicized silica | q.s. |
| Phenoxyethanol | q.s. |
| Parabens | q.s. |
| Perfume | q.s. |
| Water | ad 100 |

| | Example 28 |
|---|---|
| Ethyl palmitate | 18.0 |
| C18-38 alkyl hydroxystearoyl stearate | 5.0 |
| Hydrogenated coconut fat | 10.0 |
| Macadamia oil | 5.0 |
| Polyglyceryl-2 dipolyhydroxystearate | 2.0 |
| Polyglyceryl-3 diisostearate | 1.0 |
| Glycerol | 4.0 |
| MgSO$_4$ | 0.3 |
| Sorbic acid | q.s. |
| Parabens | q.s. |
| Perfume | q.s. |
| Water | ad 100 |

| | Example 29 |
|---|---|
| Ethyl stearate | 15.0 |
| Ceresine | 10.0 |
| Cetyl palmitate | 5.0 |
| Paraffin oil | 5.0 |
| Polyglyceryl-2 dipolyhydroxystearate | 2.0 |
| Polyglyceryl-3 diisostearate | 1.0 |
| Glycerol | 8.0 |
| MgSO$_4$ | 0.3 |
| Lactic acid | q.s. |
| Aluminum starch octenylsuccinate | q.s. |
| Parabens | q.s. |
| Perfume | q.s. |
| Water | ad 100 |

| | Example 30 |
|---|---|
| Myristyl lactate | 25.0 |
| Ceresine | 10.0 |
| Myristyl myristate | 5.0 |
| Polyethylene | 3.0 |
| Shea butter | 1.0 |
| Butyl methoxydibenzoylmethane | 1.0 |
| PEG-30 dipolyhydroxystearate | 3.0 |
| Glycerol | 10.0 |
| MgSO$_4$ | 0.3 |
| Nylon | q.s. |
| Iodopropynyl butylcarbamate | q.s. |
| Parabens | q.s. |
| Perfume | q.s. |
| Na EDTA | q.s. |
| Water | ad 100 |

| | Example 31 |
|---|---|
| Cetyl lactate | 18.0 |
| Ceresine | 2.0 |

|  | Example 31 |
| --- | --- |
| Microcrystalline wax | 4.0 |
| Polyethylene | 6.0 |
| Ethylhexyl methoxycinnamate | 1.0 |
| PEG-30 dipolyhydroxystearate | 3.0 |
| Glycerol | 6.0 |
| MgSO$_4$ | 0.3 |
| Hydrophobicized silica | q.s. |
| DMDM hydantoin | q.s. |
| Parabens | q.s. |
| Perfume | q.s. |
| Water | ad 100 |

|  | Example 32 |
| --- | --- |
| Lauryl PCA | 20.0 |
| Ceresine | 6.0 |
| Cetyl palmitate | 3.0 |
| Candelilla wax | 1.0 |
| Dimethicones | 2.0 |
| PEG-30 dipolyhydroxystearate | 4.0 |
| Glycerol | 6.0 |
| MgSO$_4$ | 0.3 |
| Hydrophobicized silica | q.s. |
| Phenoxyethanol | q.s. |
| Parabens | q.s. |
| Perfume | q.s. |
| Water | ad 100 |

|  | Example 33 |
| --- | --- |
| Myristyl myristate | 11.0 |
| Hydrogenated coconut fat | 9.0 |
| Microcrystalline wax | 5.0 |
| Polyethylene | 3.0 |
| Dicaprylyl carbonate | 5.0 |
| Polyglyceryl-2 dipolyhydroxystearate | 1.0 |
| Polyglyceryl-3 diisostearate | 2.0 |
| Glycerol | 4.0 |
| MgSO$_4$ | 0.3 |
| Mica | q.s. |
| Phenoxyethanol | q.s. |
| Parabens | q.s. |
| Perfume | q.s. |
| Water | ad 100 |

Moreover, the envelope or filling can, independently of one another, comprise auxiliaries, such as UV filters, active ingredients, sensory additives, thickeners, gel formers, dyes, color, effect or UV pigments, preservatives, antioxidants, complexing agents, flavorings, denaturants or perfume.

As described, the various fillings can be surrounded by one of the envelopes listed by way of example. The selection of fillings and envelopes represented by way of example is dependent on the particular intended use.

What is claimed is:

1. A method of applying a cosmetic ingredient and/or a dermatological ingredient to skin, wherein the method comprises at least one of rubbing and distributing on the skin in direct contact with the skin a composition consisting of one or more capsules, which capsules comprise the cosmetic ingredient and/or dermatological ingredient, the capsules having an average diameter of from 3 mm to 40 mm and comprising an envelope which is at least one of solid, semisolid and dimensionally stable and comprises at least one wax and at least one of an emulsifier, a natural polymer, and a synthetic polymer.

2. The method of claim 1, wherein the envelope is at least one of solid, semisolid and dimensionally stable up to a temperature of at least 35° C.

3. The method of claim 1, wherein the envelope comprises at least one of a microcrystalline wax, a paraffin wax, an ester wax, a glyceride wax, a fatty alcohol, and a solid emulsifier.

4. The method of claim 3, wherein the envelope comprises one or more waxes selected from cetyl palmitate, cetyl ricinoleate, beeswax, hydrogenated cocoglycerides, methyl palmitate, methyl stearate, myristyl lactate, cetyl lactate, stearyl lactate, candelilla wax, carnauba wax, paraffin wax, ceresine, ozokerite, myristyl myristate, tripalmitin, tribehenin, glyceryl palmitostearate, hydrogenated rapeseed oil, and C15-C40 alkylstearyl stearate.

5. The method of claim 1, wherein the envelope comprises constituents or constituent combinations with melting points for a melting range of the envelope at about 30° C.

6. The method of claim 1, wherein the envelope further comprises at least one of water and a polyol.

7. The method of claim 6, wherein the envelope comprises from 50% to 60% by weight of water.

8. The method of claim 1, wherein the envelope comprises one or more of a cellulose ether, polyvinylpyrrolidone, a polyacrylate, a polymethacrylate, polyethylene, nylon.

9. The method of claim 1, wherein the envelope comprises lipids which are liquid at room temperature or liquid mixtures thereof and is solidified by having water droplets incorporated therein.

10. The method of claim 1, wherein the envelope comprises a dimensionally stable lipid and emulsifier mixture which comprises dispersed water with a droplet size below 50 micrometers.

11. The method of claim 1, wherein the envelope further comprises one or more surface-active substances.

12. The method of claim 11, wherein the one or more surface-active substances comprise at least one W/O emulsifier.

13. The method of claim 1, wherein the one or more capsules have a predominantly spherical, round or ellipsoidal shape.

14. The method of claim 13, wherein each of the one or more capsules has an individual volume of from 0.1 ml to 20 ml.

15. A method of claim 1, wherein the one or more capsules have an average diameter of from 5 mm to 40 mm.

16. The method of claim 15, wherein the envelope has a thickness of from 0.001 mm to 3 mm.

17. The method of claim 1, wherein the envelope has a thickness of from 0.01 mm to 2 mm.

18. The method of claim 1, wherein the one or more capsules comprise a filling comprising one or more substances selected from cosmetic and dermatological ingredients which are at least one of solid, semisolid, pasty or liquid.

19. The method of claim 18, wherein at least one of the envelope and the filling further comprises water.

20. The method of claim 18, wherein the filling comprises at least one of an anhydrous preparation, an O/W, W/O or W/O/W emulsion, a gel, a hydrodispersion, a surfactant, and a microemulsion.

21. The method of claim 18, wherein the filling comprises an O/W emulsion.

22. The method of claim 18, wherein the filling comprises at least one of an O/W emulsion, a hydrous composition, a hydrogel, and a hydrocolloid.

23. The method of claim 18, wherein the filling comprises at least one of a detersive substance and a surfactant in solid or liquid form.

24. The method of claim 18, wherein at least one of the envelope and the filling further comprise one or more substances selected from UV filters, pigments, dyes, sensory additives, thickeners, gel formers, preservatives, antioxidants, complexing agents, flavorings, denaturants, and perfumes.

25. The method of claim 18, wherein the envelope at least one of
- melts upon at least one of rubbing and distributing it on the skin or the hair;
- becomes completely or partially liquid due to shear forces;
- dissolves in at least one of the filling and skin sebum lipids; or
- dissolves as a result of mixing filling and envelope materials, whereby the envelope it is no longer perceptible as a separate constituent besides the filling.

26. The method of claim 1, wherein the envelope comprises a cosmetic ingredient and/or a dermatological ingredient as a component thereof.

27. The method of claim 1, wherein the capsule comprises a filling and at least one of a cosmetic ingredient and a dermatological ingredient is a component of the filling.

28. The method of claim 27, wherein both the filling and the envelope comprise a cosmetic ingredient and/or a dermatological ingredient as a component thereof.

29. A method of applying a cosmetic ingredient and/or a dermatological ingredient to skin, wherein the method comprises at least one of rubbing and distributing on the skin in direct contact with the skin a composition consisting of one or more capsules, which capsules comprise the cosmetic ingredient and/or dermatological ingredient, the one or more capsules having an average diameter of from 3 mm to 40 mm and comprising (i) a filling which comprises at least one of an anhydrous preparation, an O/W, W/O or W/O/W emulsion, a gel, a hydrodispersion, and a microemulsion, and (ii) an envelope which is at least one of solid, semisolid and dimensionally stable and comprises at least one wax and at least one of an emulsifier, a natural polymer, and a synthetic polymer.

30. The method of claim 29, wherein the filling comprises an O/W emulsion.

31. The method of claim 29, wherein the envelope comprises at least one of a microcrystalline wax, a paraffin wax, an ester wax, a glyceride wax, a fatty alcohol, and a solid emulsifier.

32. The method of claim 29, wherein the envelope further comprises at least one of water and a polyol.

33. The method of claim 29, wherein the envelope comprises lipids which are liquid at room temperature or liquid mixtures thereof and is solidified by having water droplets incorporated therein.

34. The method of claim 29, wherein the envelope further comprises one or more surface-active substances.

35. The method of claim 29, wherein the filling comprises at least one of an O/W emulsion, a hydrodispersion, and hydrogel.

36. The method of claim 29, wherein the envelope comprises a cosmetic ingredient and/or a dermatological ingredient as a component thereof.

37. The method of claim 29, wherein the capsule comprises a filling and a cosmetic ingredient and/or a dermatological ingredient is a component of the filling.

38. The method of claim 37, wherein both the filling and the envelope comprise a cosmetic ingredient and/or a dermatological ingredient as a component thereof.

39. The method of claim 1, wherein the one or more capsules are provided as a plurality of capsules in a packaging.

40. The method of claim 1, wherein the one or more capsules are provided packaged individually or in a number of two or more in a blister pack.

41. The method of claim 29, wherein at least two capsules which differ in at least one of their appearance, their ingredients, and their purpose are employed.

42. The method of claim 41, wherein the at least two capsules differ in at least their color.

43. The method of claim 29, wherein the one or more capsules have a predominantly spherical, round or ellipsoidal shape and each of the capsules has an individual volume of from 0.1 ml to 20 ml.

44. A method of claim 29, wherein the one or more capsules have an average diameter of from 5 mm and 40 mm.

* * * * *